(12) United States Patent
Chuang

(10) Patent No.: US 10,634,666 B2
(45) Date of Patent: Apr. 28, 2020

(54) NON-OBESE DIABETES MICE AND ITS APPLICATIONS

(71) Applicant: TAIPEI MEDICAL UNIVERSITY, Taipei (TW)

(72) Inventor: Kuo-Hsiang Chuang, Taipei (TW)

(73) Assignee: TAIPEI MEDICAL UNIVERSITY, Taipei (TW)

( * ) Notice: Subject to any disclaimer, the term of this patent is extended or adjusted under 35 U.S.C. 154(b) by 208 days.

(21) Appl. No.: 15/364,228

(22) Filed: Nov. 29, 2016

(65) Prior Publication Data

US 2018/0146649 A1 May 31, 2018

(51) Int. Cl.
*A01K 67/027* (2006.01)
*G01N 33/50* (2006.01)
*C07K 16/44* (2006.01)

(52) U.S. Cl.
CPC ..... *G01N 33/5088* (2013.01); *A01K 67/0275* (2013.01); *C07K 16/44* (2013.01); *A01K 2217/052* (2013.01); *A01K 2217/206* (2013.01); *A01K 2227/105* (2013.01); *A01K 2267/0362* (2013.01); *A01K 2267/0393* (2013.01)

(58) Field of Classification Search
CPC ................................................ A01K 67/0275
See application file for complete search history.

(56) References Cited

FOREIGN PATENT DOCUMENTS

TW         I390040 B1       3/2013

OTHER PUBLICATIONS

Leiter Eh., 1993, ILAR Journal, vol. 35(1), pp. 4-14 (Year: 1993).*
Belancio Vp, 2011, Anal. Biochem., vol. 417(1), pp. 159-161 (Year: 2011).*
Mahmoud et al. (2011, J. Virology, vol. 85, pp. 9268-9275 (Year: 2011).*
Chuang, Kuo-Hsiang, "Expressing membrane antibody reporter in the islet cells of non-obese diabetic mice to non-invasive image the disease progression of autoimmune diabetes," Fourth International Conference on Translational Medicine, Oct. 26-28, 2015.
Chuang, Kuo-Hsing et al., "Development of a Universal Anti-Polyethylene Glycol Reporter Gene for Noninvasive Imaging of PEGylated Probes," The Journal of Nuclear medicine, 2010, pp. 933-941, vol. 51, No. 6.
Contag, Pamela R., et al., "Bioluminescent indicators in living mammals," Nature Medicine, Feb. 1998, pp. 245-247, vol. 4, No. 2.
Grzech, Marjeta, et al., "Specific transgene expression in mouse pancreatic β-cells under the control of the porcine insulin promoter,".
Molecular and Cellular Endocrinology, 315 (2010), pp. 219-224.
Sung, Hsiang-Hsuan et al., "Transgenic Expression of Decoy Receptor 3 Protects Islets from Spontaneous and Chemical-induced Autoimmune Destruction in Nonobese Diabetic Mice," The Journal of Experimental Medicine, Apr. 19, 2004, pp. 1143-1151, vol. 199, No. 8.
Office Action issued in related Taiwanese Application No. 10620689010, dated Jun. 30, 2016, 7 pgs.

* cited by examiner

*Primary Examiner* — Thaian N. Ton
*Assistant Examiner* — David A. Montanari
(74) *Attorney, Agent, or Firm* — Duane Morris LLP

(57) ABSTRACT

The invention relates to a novel non-obese diabetic (NOD) mouse and its application. Particularly, the invention relates to a NOD mouse specifically expressing anti-polyethylene glycol membrane antibody reporter (anti-PEG reporter) in the NOD mouse.

8 Claims, 16 Drawing Sheets
(14 of 16 Drawing Sheet(s) Filed in Color)
Specification includes a Sequence Listing.

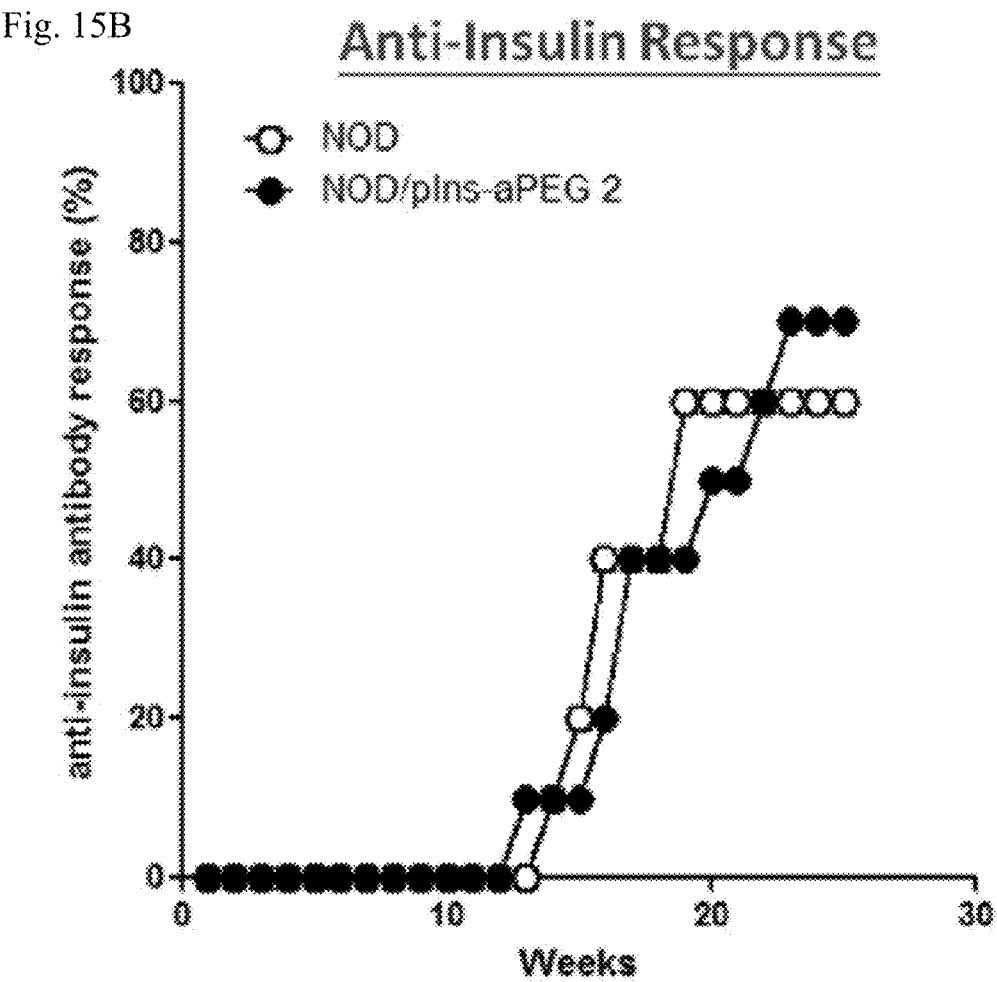

NON-OBESE DIABETES MICE AND ITS APPLICATIONS

FIELD OF THE INVENTION

The invention relates to a novel non-obese diabetic (NOD) mouse and its application. Particularly, the invention relates to a NOD mouse specifically expressing anti-polyethylene glycol membrane antibody reporter (anti-PEG reporter) in the NOD mouse.

BACKGROUND OF THE INVENTION

Transgenic mice are reported to develop diabetes at a similar or higher rate and kinetics as wildtype controls. Transgenic mice may be useful in studies of diabetes and pancreatic beta islet cell biology. NOD mice are used as an animal model for type 1 diabetes. NOD mice exhibit a susceptibility to spontaneous development of autoimmune insulin dependent diabetes mellitus (IDDM). Genetic Loci associated with susceptibility to IDDM have been identified in the NOD mouse strain through the development of congenic mouse strains, which have identified several insulin dependent diabetes (Idd) loci. In view of the fact that the NOD mice' unique genetic factors and pathological mechanism are similar to human type 1 diabetes, NOD mice are an important animal model in exploring IDDM mechanism and evaluating various therapeutic strategies.

However, to explore whether apoptosis progresses in pancreatic beta-cells (insulitis), a number of NOD mice should be sacrificed to obtain a series of pancreas islet sections at continuous time points. As a result, researches cannot continuously observe pathological process in one mouse and use the method of monitoring blood sugar of NOD mice to evaluate progress of diabetes; only late-stage diabetes can be measured. Moreover, the incidence of spontaneous diabetes in the NOD mouse is 60-80% in females and 20-30% in males. Onset of diabetes also varies between males and females: commonly, onset is delayed in males by several weeks. Therefore, the variations in animal gender and environmental and experimental conditions would impact the research results of diabetes. For example, NOD.Cg-Tg (Ins1-EGFP)1Hara/QtngJ (also known as: MIP-GFP (line 1), NOD.B6-MIP-GFP) is a congenic NOD mouse ice hemizygous for the MIP-GFP transgene, which has EGFP fluorescence in tissues where insulin I is normally detected, specifically in pancreatic beta-cells. However, this NOD transgenic mouse only can be used in optical imaging system and the observation on diabetes can be performed only after the mouse is sacrificed. Moreover, the GFP originated from jellyfish may cause immune rejection when the pancreatic islets of NOD mouse are transplanted to normal mouse. U.S. Pat. No. 8,507,207 provides a reporter gene system, and in particular relates to a method for using a recombinant nucleotide sequence encoding an anti-polyethylene glycol recombinant single chain membrane antibody as a reporter gene to monitor presence and distribution of a gene and a cell.

However, there is a need to develop a NOD mouse that can be used in continuous observation of diabetes pathological process and evaluation of drug treatment of type I diabetes.

SUMMARY OF THE INVENTION

Expressing a reporter gene in the pancreatic islet of non-obese diabetic mice (NOD mice) allows researchers real-time monitoring the processes of islet loss by noninvasive imaging systems, overcoming the defect of traditional method in which researchers need to sacrifice lots of NOD mice to observe the insulitis in pancreatic islet section. The invention successfully develops a NOD/pIns-αPEG mouse which stably expresses the anti-PEG reporter in its pancreatic islets by using an insulin promoter. The PEG-NIR797 fluorescent probe can specifically accumulate at the pancreatic islet region of NOD/pIns-αPEG mice but not control NOD mice, assisting researchers in conveniently and accurately tracing the process of islet loss and further investigating the islet-protective effects of drugs or genes by optical imaging system. Importantly, expressing the anti-PEG reporter in the pancreatic islet of NOD/pIns-αPEG mice does not affect the islet size, insulin secretion, and the disease progression of type 1 diabetes. The NOD/pIns-αPEG mice may help researchers easily tracing the disease progression of type1 diabetes by noninvasive imaging systems, further providing a valuable tool for worldwide pharmaceutical companies and drug research institutes to screen and evaluate the diabetes drugs.

The invention provides a transgenic gene construct encoding anti-PEG reporter gene, comprising a polynucleotide comprising, from 5' to 3' sequence, a human insulin promoter having a nucleotide sequence of SEQ ID NO:1 or a substantially same nucleotide sequence thereof, a first exon of human insulin gene having a nucleotide sequence of SEQ ID NO:2 or a substantially same nucleotide sequence thereof, a first intron of human insulin gene having a nucleotide sequence of SEQ ID NO:3 or a substantially same nucleotide sequence thereof, a second exon of human insulin gene having a nucleotide sequence of SEQ ID NO: 4 or a substantially same nucleotide sequence thereof, a second intron of rabbit beta globin gene having a nucleotide sequence of SEQ ID NO:5 or a substantially same nucleotide sequence thereof, an anti-PEG reporter gene having a nucleotide sequence of SEQ ID NO:6 or a substantially same nucleotide sequence thereof and a third intron of rabbit beta globin gene having SEQ ID NO:7 or a substantially same nucleotide sequence thereof, which are operably linked to each other.

The invention also provides a vector comprising the transgenic gene construct of the invention or a cell comprising the above-mentioned vector.

The invention also provides a chimeric NOD mouse, wherein the genome of the NOD mouse comprises a transgenic gene construct of the invention incorporated into a site at chromosome 11 of the mouse. In one embodiment, the site is chr11:14970958 at chromosome 11 of the mouse.

The invention also provides applications including using the chimeric NOD mouse of the invention to screen a candidate agent or a gene therapy for treatment or prevention of type 1 diabetes and screen a candidate agent or a gene against rejection in transplantation of pancreatic islets.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 15A and 15B show the incidence of diabetes and the anti-insulin autoantibody reaction in the NOD/pIns-αPEG mice and NOD mice. 15A The blood glucose value of NOD/pIns-αPEG mice (n=20) and NOD mice (n=20) were monitored weekly after 5 weeks from birth; it is determined as an incidence of diabetes if the blood glucose detected is over 200 mg/L in two consecutive weeks. 15B The blood of NOD/pIns-αPEG mice (n=10) and NOD mice (n=10) was obtained weekly after 5 weeks from birth; whether anti-GAD65 auto-antibodies are produced in the blood is detected by an anti-GAD65 ELISA kit.

DETAILED DESCRIPTION OF THE INVENTION

Figure 1:
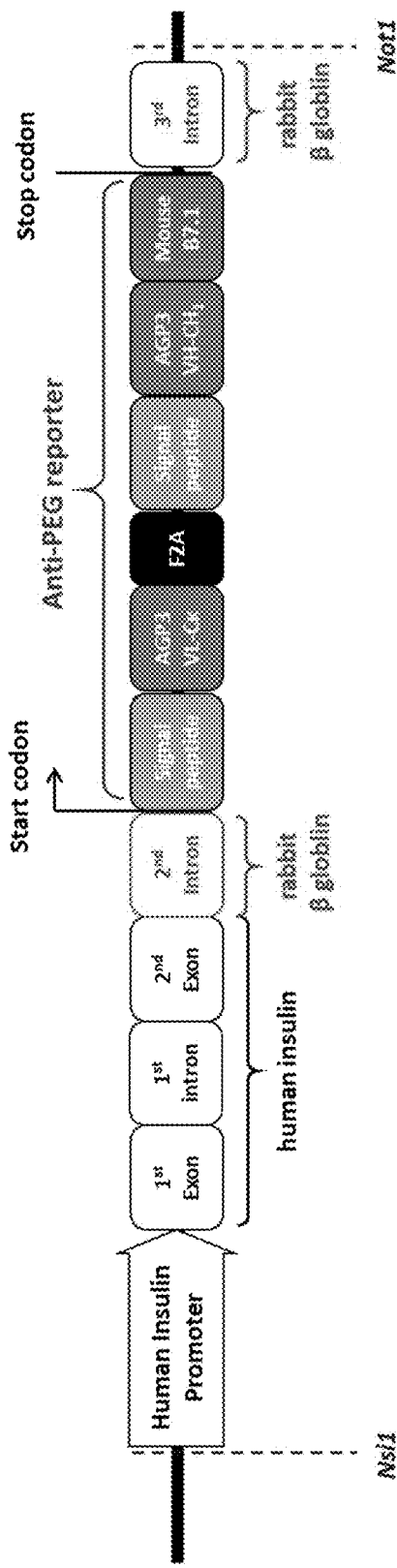
FIG. 1 shows the schematic diagram of the whole transgenic gene construct of the invention. The whole transgenic gene includes, from 5' to 3' sequence, a human insulin promoter, a first exon of human insulin gene, a first intron of human insulin gene, a second exon of human insulin gene, a second intron of rabbit beta-globin gene, an anti-PEG reporter gene (including, from 5' to 3' sequence, an immunoglobulin signal peptide, a VL-Ck fragment of anti-PEG antibody AGP3, an internal ribosomal entry site, an immunoglobulin signal peptide, a VH-CH1 fragment of anti-PEG antibody AGP3, and a C-like extracellular-transmembrane-cytosolic domains of the mouse B7-1 antigen), and a third intron of rabbit beta-globin gene.

The invention provides a non-obese diabetes mouse and its application in non-invasive imaging the process of pancreatic islet loss therein.

As used herein unless indicated otherwise terms have meanings as generally used in the science parlance which may differ from colloquial common usage.

A gene should be interpreted broadly to include transcribed as well as non-transcribed regions.

By "encoding" or "encoded," with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons.

As used herein, the term "transgenic rodent" is intended to include a mouse in which one or more of the cells of the mouse contain heterologous nucleic acid encoding an anti-PEG reporter. The heterologous nucleic acid is introduced into the rodent by way of human intervention, such as by transgenic techniques well known in the art. Preferably, the heterologous nucleic acid is integrated within a chromosome in the cell.

As used herein, the term "transgene" means a nucleic acid sequence encoding an anti-PEG reporter.

As used herein, the term "nucleic acid" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides.

As used herein, the term "degenerate sequence" refers to a sequence having degeneracy of codons that is the redundancy of the genetic code, exhibited as the multiplicity of three-base pair codon combinations that specify an amino acid. The degeneracy of the genetic code is what accounts for the existence of synonymous mutations.

As used herein, the term "promoter" refers to a DNA sequence capable of controlling the transcription of the nucleotide sequence of interest into mRNA, when ligated to a nucleotide sequence of interest.

As used herein, the term "operably linked" is meant that a DNA sequence and a regulatory sequence(s) are connected in such a way as to permit gene expression when the appropriate molecules (e.g., transcriptional activator proteins) are bound to the regulatory sequence(s).

As used herein, the term "transgenic gene construct" refers to a nucleic acid molecule, e.g., a vector, containing the subject gene, e.g., the anti-PEG reporter transgene, operably linked in a manner capable of expressing the gene in a host cell. As used herein, the term "nucleic acid" refers to polynucleotides such as deoxyribonucleic acid (DNA), and, where appropriate, ribonucleic acid (RNA). As used herein the term also encompasses analogs of either RNA or DNA made from nucleotide analogs, and, as applicable to the embodiment being described, single-stranded (such as sense or antisense) and double-stranded polynucleotides.

As used, herein, the term "recombinant vector", which describes a vector capable of expressing a protein or RNA of interest in a suitable host cell, refers to a genetic construct that comprises essential regulatory elements to which a gene insert, is operably linked in such a manner as to be expressed in a host cell.

As used herein, the term "transcriptional regulatory sequence" refers to DNA sequences, such as initiation signals, enhancers, and promoters, which induce or control transcription of protein coding sequences with which they are operably linked.

As used herein, the term "chimeric" (e.g., "chimeric animal" or "chimeric pancreas") is meant to describe an organ or animal comprising xenogeneic tissues or cells.

As used herein, the term "candidate agents" is meant to include synthetic, naturally occurring, or recombinantly produced molecules (e.g., small molecule; drugs; peptides; antibodies (including antigen-binding antibody fragments) or other immunotherapeutic agents; endogenous factors present in eukaryotic or prokaryotic cells (e.g., polypeptides, plant extracts, and the like)); etc.). Of particular interest are screening assays for agents that have a low toxicity for human cells."

In one aspect, the invention provides a transgenic gene construct encoding anti-PEG reporter gene, comprising a polynucleotide comprising, from 5' to 3' sequence, a human insulin promoter having a nucleotide sequence of SEQ ID NO:1 or a substantially same nucleotide sequence thereof, a first exon of human insulin gene having a nucleotide sequence of SEQ ID NO:2 or a substantially same nucleotide sequence thereof, a first intron of human insulin gene having a nucleotide sequence of SEQ ID NO:3 or a substantially same nucleotide sequence thereof, a second exon of human insulin gene having a nucleotide sequence of SEQ ID NO:4 or a substantially same nucleotide sequence thereof, a second intron of rabbit beta globin gene having a nucleotide sequence of SEQ ID NO:5 or a substantially same nucleotide sequence thereof, an anti-PEG reporter gene having a nucleotide sequence of SEQ ID NO:6 or a substantially same nucleotide sequence thereof and a third intron of rabbit beta globin gene having SEQ ID NO:7 or a substantially same nucleotide sequence thereof, which are operably linked to each other.

The transgenic gene construct of the invention comprises a human insulin promoter (1620 bp), a first exon (partial human insulin gene, 42 bp), a first intron (human insulin gene, 178 bp), a second exon (partial human insulin gene, 50 bp), a second intron (rabbit 1 globin gene, 573 bp), an anti-PEG reporter gene, and a third intron (rabbit 1 globin gene, 449 bp).

In one embodiment, the anti-PEG reporter gene comprises a nucleotide gene of SEQ ID NO:6.

In one embodiment, the substantially same nucleotide sequence is a degenerate sequence.

The sequences of the human insulin promoter, the first exon, the first intron, the second exon, the second intron, the anti-PEG reporter gene and the third intron are listed below.

```
Human insulin promoter (1620 bp)
                                        (SEQ ID NO: 1)
gatcctggatctcagctccctggccgacaacactggcaaactcctactca tccacgaaggccctcctgggcatggtggtccttcccagcctggcagtctg ttcctcacacaccttgttagtgcccagcccctgaggttgcagctggggt gtctctgaagggctgtgagcccccaggaagccctgggaagtgcctgcct tgcctcccccggccctgccagcgcctggctctgccctcctacctgggct cccccatccagcctccctccctacacactcctctcaaggaggcacccat gtcctctccagctgccgggcctcagagcactgtggcgtcctggggcagcc accgcatgtcctgctgtggcatggctcagggtggaaagggcggaagggag gggtcctgcagatagctggtgcccactaccaaacccgctcggggcaggag agccaaaggctgggtgtgtgcagagcggccccgagaggttccgaggctga ggccagggtgggacatagggatgcgagggccggggcacaggatactcca acctgcctgccccatggtctcatcctcctgcttctgggacctcctgatc tttgccctttgtttgataattaggcaggtaggggctgcaggcagcaggt ttcggagcccatgccccctcttccatgggtcaggttttggacctccaggtg ctttgttctggggagtttgggagggccggaggggtgtacccccagggctc agcccagatgacactatgggggtgatggtgtcatgggacctggccaggag aggggagatgggctcccagaagaggagtgggggctgagagggtgcctggg gggccaggacggagctgggccagtgcacagcttcccacacctgcccaccc ccagagtcctgccgccaccccagatcacacggaagatgaggtccgagtg gcctgctgaggacttgctgcttgtcccccaggtccccaggtcatgccctcc ttctgccaccctggggagctgagggcctcagctggggctgctgtctaagg cagggtgggcaatttaaggcagccagcaggaggggaccctcctcactc ccactctcccaccccaccaccttggcccatccatggcggcatcttgggc catccgggactggggacaggggtcctggggacaggggtctgaggacaggg gtgtgggcacaggggtcctggggacaggggtcctggggacaggggtcctg gggacagggtctggggacaacagcgcaaagaccccccccctgcagcctc catctctcctggtctaatgtggaaagtggcccaggtgagggctttgctct cctggagacatttgccccccagctgtgagcagggacaggtctggccaccgg gcccctggttaagactctaatgccccgctggtcctgaggaagaggtgctg acgaccaaggagatcttcccacagcccagcaccagggaaatggtccgga aattgcagcctcagcccccagccatctgccgaccccccaccccagccct aatgggccaggcggcaggggttgacaggtaggggagatgggctctgagac tataaagccagcgggggcccagcagccctc
```

```
First exon (partial human insulin gene, 42 bp)
                                        (SEQ ID NO: 2)
agccctccaggacaggctgcatcagaagaggccatcaagcag First intron (human insulin gene, 178 bp)
                                        (SEQ ID NO: 3)
gtctgttccaagggcctttgcgtcaggtgggctcagggttccagggtggc tggaccccaggccccagctctgcagcagggaggacgtggctgggctcgtg aagcatgtgggggtgagcccaggggcccaaggcagggcacctgccttca gcctgcctcagccctgcctgtctcccag Second exon (partial human insulin gene, 50 bp)
                                        (SEQ ID NO: 4)
atcactgtccttctgcacctgcagggatcggggatcctgagaacttcagg Second intron (rabbit β globin gene, 573 bp)
                                        (SEQ ID NO: 5)
gtgagtttggggaccatgattgttattattttcgctattgtaaaattcat gttatatggagggggcaaagttttcagggtgttgtttagaatgggaagat gtccatgtatcaccatggaccctcatgataattttgtttctttcactttc tactctgttgacaaccattgtctcctcttattttcttttcattttctgta acttttcgttaaactttagcttgcatttgtaacgaatttttaaattcac ttttgtttatttgtcagattgtaagtactttctctaatcactttttttc aaggcaatcagggtatattatattgtacttcagcacagttttagagaaca attgttataattaaatgataaggtagaatatttctgcatataaattctgg ctggcgtggaaatattcttattggtagaaacaactacaccctggtcatca tcctgccttttctctttatggttacaatgatatacactgtttgagatgagg ataaaatactctgagtccaaaccgggcccctctgctaaccatgttcatgc cttcttctctttcctacag Anti-PEG reporter gene (2574 bp)
                                        (SEQ ID NO: 6)
atggagacagacacactcctgctatgggtactgctgctctgggttccagg ttccactggtgacggaggggccgatattgtgttgacgcaggctgcattct ccaatccagtcactcttggaacatcagcttccatctcctgcaggtctagt aagagtctcctacatagtaatggcatcacttatttgtattggtatctgca gaagccaggccagtctcctcagctcctgatttatcagatgtccaaccttg cctcaggagtcccagacaggttcagtagcagtgggtcaggaactgatttc acactgagaatcagcagagtggaggctgaggatgtgggtgtttattactg tgctcaaaatctagaactattcacgttcggctcggggacaaagttggaaa taaaacgggctgatgctgcaccaactgtatccatcttcccaccatccagt gagcagttaacatctggaggtgcctcagtcgtgtgcttcttgaacaactt ctaccccaaagacatcaatgtcaagtggaagattgatggcagtgaacgac aaaatggcgttgaacagttggactgatcaggacagcaaagacagcaccta cagcatgagcagcaccctcacgttgaccaaggacgagtatgaacgacata acagctatacctgtgaggccactcacaagacatcaacttcacccattgtc aagagcttcaacaggaatgagtgttagctcgagggatccgcccctctccc tccccccccctaacgttactggccgaagccgcttggaataaggccggtg tgcgtttgtctatatgttattttccaccatattgccgtcttttggcaatg
```

-continued
tgagggcccggaaacctggccctgtcttcttgacgagcattcctaggggt ctttcccctctcgccaaaggaatgcaaggtctgttgaatgtcgtgaagga agcagttcctctggaagcttcttgaagacaaacaacgtctgtagcgaccc tttgcaggcagcggaaccccccacctggcgacaggtgcctctgcggccaa aagccacgtgtataagatacacctgcaaaggcggcacaacccccagtgcca cgttgtgagttggatagttgtggaaagagtcaaatggctctcctcaagcg tattcaacaaggggctgaaggatgcccagaaggtaccccattgtatggga tctgatctggggcctcggtgcacatgctttacatgtgtttagtcgaggtt aaaaaaacgtctaggcccccccgaaccacggggacgtggttttcctttgaa aaacacgatgataatatggccacaaccatggagacagacacactcctgct atgggtactgctgctctgggttccaggttccactggtgacagatctgaag tgcagctggtggagtctgggggaggcttagtgaagcctggagggtccctg aaactctcctgtgcagcctctggattcactttcagtgactattacatgta ttgggttcgccagactccggaaaagaggctggagtgggtcgcaaccatta gtgatgatggtacttacacctactatccacacagtgtgaaggggcgattc accatctccagagacagtgccaagaacaacctgtacctgcaattgagcag tctgaagtctgaggacacagccatgtattactgtgcaagaaatgatgcta gggggactactggggtcaaggaacctcagtcaccgtctcctcagagagt cagtccttcccaaatgtcttcccctcgtctcctgcgagagcccctgtc tgataagaatctggtggccatgggctgcctggcccgggacttcctgccca gcaccatttccttcacctggaactaccagaacaacactgaagtcatccag ggtatcagaaccttcccaacactgaggacaggggggcaagtacctagccac ctcgcaggtgttgctgtctcccaagagcatccttgaaggttcagatgaat acctggtatgcgaaatccactacggaggcaaaaacagagatctgcatgtg cccattccagctgtcgcagaggtcgacgctgacttctctaccccaacat aactgagtctggaaacccatctgcagacactaaaaggattacctgattga tccgggggtttcccaaagcctcgcttctcttggttggaaaatggaagaga attacctggcatcaatacgacaatttcccaggatcctgaatctgaattgt acaccattagtagccaactagatttcaatacgactcgcaaccacaccatt aagtgtctcattaaatatggagatgctcacgtgtcagaggacttcacctg ggaaaaaccccagaagaccctcctgatagcaagaacacacttgtgctct ttggggcaggattcggcgcagtaataacagtcgtcgtcatcgttgtcatc atcaaatgcttctgtaagcacagaagctgtttcagaagaaatgaggcaag cagagaaacaaacaacagccttaccttcgggcctgaagaagcattagctg aacagaccgtcttcctttag Third intron (rabbit β globin gene, 449 bp)
(SEQ ID NO: 7)
gatcttttccctctgccaaaaattatggggacatcatgaagcccctga gcatctgacttctggctaataaaggaaatttattttcattgcaatagtgt gttggaattttttgtgtctctcactcggaaggacatatgggagggcaaat catttaaaacatcagaatgagtatttggtttagagtttggcaacatatgc ccatatgctggctgccatgaacaaaggttggctataaagaggtcatcagt -continued
atatgaaacagcccctgctgtccattccttattccatagaaaagccttg acttgaggttagatttttttatattttgttttgtgttattttttctttt aacatccctaaaatttccttacatgttttactagccagattttcctcc tctcctgactactcccagtcatagctgtccctcttctcttatggagatc As employed herein, the term "substantially the same nucleotide sequence" refers to DNA having sufficient identity to the reference polynucleotide, such that it will hybridize to the reference nucleotide under moderately stringent, or higher stringency, hybridization conditions. DNA having "substantially the same nucleotide sequence" as the reference nucleotide sequence, can have an identity ranging from at least 60% to at least 95% with respect to the reference nucleotide sequence.

The moderately stringent hybridization refers to conditions that permit a target-nucleic acid to bind a complementary nucleic acid. The hybridized nucleic acids will generally have an identity within a range of at least about 60% to at least about 95%. Moderately stringent conditions are conditions equivalent to hybridization in 50% formamide, 5×Denhart's solution, 5× saline sodium phosphate EDTA buffer (SSPE), 0.2% SDS (Aldrich) at about 42° C. followed by washing in 0.2 SSPE, 0.2% SDS (Aldrich), at about 42° C. High stringency hybridization refers to conditions that permit hybridization of only those nucleic acid sequences that form stable hybrids in 0.018 M NaCl at about 65° C., for example, if a hybrid is not stable in 0.018 M NaCl at about 65° C., it will not be stable under high stringency conditions, as contemplated herein. High stringency conditions can be provided, for example, by hybridization in 50% formamide, 5×Denhart's solution, 5×SSPE, 0.2% SDS at about 42° C., followed by washing in 0.1×SSPE, and 0.1% SDS at about 65° C.

The anti-PEG reporter gene is constructed according to "Kuo-Hsing Chuang et al., The Journal of Nuclear medicine, 2010, Vol. 51, No. 6, pp. 933-941". The anti-PEG reporter consists of the Fab fragment of a mouse anti-PEG monoclonal antibody, AGP3, fused to the C-like extracellular-transmembrane-cytosolic domains of the mouse B7-1 receptor.

The transgenic gene construct of the invention is constructed according to general cloning technology. The first noncoding exon followed by the first intron and 50 bp of the second noncoding exon are preserved to ensure the stringency of the insulin promoter. The intron of rabbit β-globin gene is introduced adjacent to the second exon. A forward primer located in the second intron of the rabbit beta globin gene and a backward primer in the coding region of VL-CK fragment of the anti-PEG reporter gene were designed to determine the transcription of transgene in RT PCR and to detect the existence of anti-PEG reporter transgene from genomic PCR. Only anti-PEG reporter gene can express anti-PEG reporter protein.

If desired, the transgenic gene construct of the invention can be engineered to be operatively linked to appropriate expression elements such as enhancers to allow expression of a genetic element in the DNA construct in an appropriate cell or tissue. The use of the expression control mechanisms allows for the targeted delivery and expression of the gene of interest. For example, the constructs of the present invention may be constructed using an expression cassette which includes in the 5'-3' direction of transcription, a transcriptional and translational initiation region associated with gene expression in tissue, DNA encoding an anti-PEG reporter and a transcriptional and translational termination region functional in the host animal. The transcriptional initiation region can be endogenous to the host animal or foreign or exogenous to the host animal. The transgenic gene constructs described herein may be incorporated into vectors for propagation or transfection into appropriate cells to generate.

In another aspect, the invention provides a vector comprising the transgenic gene construct of the invention or a cell comprising the above-mentioned vector.

Vectors can contain a regulatory element that provides tissue specific or inducible expression of an operatively linked nucleic acid. One skilled in the art can readily determine an appropriate enhancer that allows expression of anti-PEG reporter in a desired genome.

For example, the transgenic gene construct comprising an anti-PEG reporter is cloned into a vector to form pIns-αPEG plasmid having a polynucleotide encoding a human insulin promoter by general cloning techniques; see, for example, pLNCX-eB7 retroviral vector; for example, see "Kuo-Hsiang Chuang et al., The Journal of Nuclear Medicine, 2010, Vol. 51, No. 6, pp. 933-941; for example, pIns vector; for example, see "Hsiang-Hsuan Sung et al.", The Journal of Experimental Medicine, 2004, Vol. 199, No. 8, pp. 1143-1151.

In another aspect, the invention provides a chimeric NOD mouse, wherein the genome of the NOD mouse comprises a transgenic gene construct of the invention. In one embodiment, the transgenic gene construct of the invention is incorporated into a site at chromosome 11 of the mouse. In one embodiment, the transgenic gene construct of the invention is incorporated into the site chr11:14970958 at chromosome 11 of the mouse.

The transgenic gene construct can be integrated into the genome of a transgenic NOD mouse by any method known to those skilled in the art. The transgenic gene construct can be introduced into pluripotent cells, such as ES cells, by any method that will permit the introduced molecule to undergo recombination at its regions of homology. Techniques that can be used include, but are not limited to, calcium phosphate/DNA co-precipitates, microinjection of DNA into the nucleus, electroporation, bacterial protoplast fusion with intact cells, transfection, and polycations, (e.g., polybrene, polyornithine, etc.).

For example, the zygote is a good target for microinjection, and methods of microinjecting zygotes are well known. The vector containing the transgenic gene construct is micro-injected into a fertilized ovum to produce a NOD/pIns-αPEG mice using microinjection techniques known in the art; for example, see Marj eta Grzech et al., Molecular and Cellular Endocrinology, 315 (2010), pp. 219-224.

Particularly, transgenic mice are generated as follows: pIns-αPEG plasmid is digested with Nsi I and Not I enzymes. A fragment containing the human insulin promoter, anti-PEG reporter gene and polyadenylation signal is then gel purified. Transgenic mice are generated by standard pronuclear injection into mouse embryos. In brief, during pronuclear microinjection, the anti-PEG reporter gene cassette DNA is introduced directly into the mouse egg just after fertilization. The DNA tends to integrate as many tandem arranged copies at a random position in the genome, often after one or two cell divisions have occurred. Therefore, the resulting mouse is only partially transgenic. If the transgenic cells contribute to the germ line, then some transgenic eggs or sperm will be produced and the next generation of mice will be transgenic.

In another aspect, the invention provides a method of determining the effect of a target gene on pancreatic islet cell apoptosis in a NOD mouse of the invention, the method comprising: hybridizing the NOD mouse of the invention with a NOD transgenic mouse carrying the target gene; detecting a signal emitted by the NOD transgenic mouse at a first time point; administering a dose of PEG-imaging agent to the NOD mouse; and determining the change in signal emitted by the NOD mouse at subsequent different time points; wherein the gene is determined to have an effect on the pancreatic islet cell apoptosis if the change in signal emitted by the NOD mouse is significantly different than the signal emitted at the first time point.

Transgenic mice that expressed anti-PEG reporter are generated. In these animals, the reporter gene, anti-PEG reporter, was linked to a human insulin promoter, thus driving expression of anti-PEG reporter in pancreatic islet cells. Systemic injection of the PEG imaging agent generates a detectable and quantifiable signal from a living mouse. This model successfully quantitatively monitors a pancreatic islet cell apoptosis.

Advances in detector technology have led to substantial improvement in sensitivity and image quality. The PEG-imaging agent may be PEG-NIR797, PEG-SPIO or PEG-124I. The signal detection may be optical imaging, MRI or micro-PET.

Of the imaging modalities available, optical techniques based on bioluminescence or fluorescence have emerged as the most accessible and easily manipulated. Bioluminescent imaging (BLI) is characterized by remarkable sensitivity, as background luminescence (noise) from tissues is exceedingly low.

The monitoring of expression of expression cassettes using non-invasive whole animal imaging has been described (Contag, P., et al, Nature Medicine 4(2):245-247, 1998). Such imaging typically uses at least one photo detector device element, for example, a charge-coupled device (CCD) camera.

In another aspect, the invention provides a method for screening a candidate agent or a gene therapy for treatment or prevention of type 1 diabetes, comprising administering a candidate agent or a gene to a NOD mouse of the invention; administering a dose of PEG-imaging agent to the NOD mouse at different time points; and determining the signal emitted by the NOD mouse at the different time points; wherein the signal emitted by the NOD mouse is unchanged or increased over time relative to the signal prior to candidate agent administration indicates the candidate agent or gene has an effect on the treatment or prevention of type 1 diabetes.

In a further aspect, the invention provides a method for screening a candidate agent or a gene against rejection in transplantation of pancreatic islets, comprising transplanting a pancreatic islet obtained from the NOD mouse of the invention to a receipt mouse, administering a candidate agent or a gene against rejection to the receipt mouse; administering a dose of PEG-imaging agent to the NOD mouse at different time points; and determining the signal emitted by the NOD mouse at the different time points; wherein the signal emitted by the NOD mouse is unchanged or increased over time relative to the signal prior to candidate agent administration indicates the candidate agent or gene has an effect against transplantation rejection.

The NOD mouse of the invention can be used in a variety of other screening assays. For example, any of a variety of candidate agents suspected of treatment or prevention of type 1 diabetes as well as the appropriate antagonists and blocking therapeutic agents, or a candidate agent or a gene against rejection in transplantation of pancreatic islets can be screened by administration to the NOD mouse and assessing the effect of these agents.

Candidate agents encompass numerous chemical classes, though typically they are organic molecules, preferably small organic compounds. Candidate agents are also found among biomolecules including, but not limited to: peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Additionally, natural or synthetically produced libraries and compounds are readily modified through conventional chemical, physical and biochemical means, and may be used to produce combinatorial libraries.

The candidate agent can be administered in any manner desired and/or appropriate for delivery of the agent in order to affect a desired result. For example, the candidate agent can be administered by injection (e.g., by injection intravenously, intramuscularly, subcutaneously, or directly into the tissue in which the desired affect is to be achieved), orally, or by any other desirable means. Normally, the in vivo screen will involve a number of animals receiving varying amounts and concentrations of the candidate agent (from no agent to an amount of agent that approaches an upper limit of the amount that can be delivered successfully to the animal), and may include delivery of the agent in different formulations and routes. The agents can be administered singly or can be combined in combinations of two or more, especially where administration of a combination of agents may result in a synergistic effect.

In a further aspect, the invention provides a method for evaluating survival of a transplanted pancreatic islet, comprising transplanting a pancreatic islet obtained from the NOD mouse of the invention to a receipt mouse, administering a dose of PEG-imaging agent to the NOD mouse at different time points; and determining the signal emitted by the NOD mouse at the different time points; wherein the survival of the transplanted pancreatic islet is poor if the signal emitted by the NOD mouse is decreased over time.

Uses of the NOD mouse of the invention that are variations upon or in addition to those described above will be readily apparent to the ordinarily skilled artisan upon reading of the present specification.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed.

EXAMPLES

Example 1 Preparation of the Transgenic Gene Construct of the Invention

To construct pIns-anti-PEG reporter gene as shown in FIG. 1, the VL-Ck and VH-CH1 genes of anti-PEG reporter were joined by an internal ribosome entry site (IRES) and fused to the complementary DNA sequence encoding the C-like extracellular-transmembrane-cytosolic domains of the mouse B7.1 antigen (B7) to form anti-PEG reporter gene. The anti-PEG reporter gene was sliced and ligated into a vector with a human insulin promoter to construct a pIns-αPEG plasmid. FIG. 1 shows the schematic diagram of the whole transgenic gene construct of the invention.

Figure 2A:
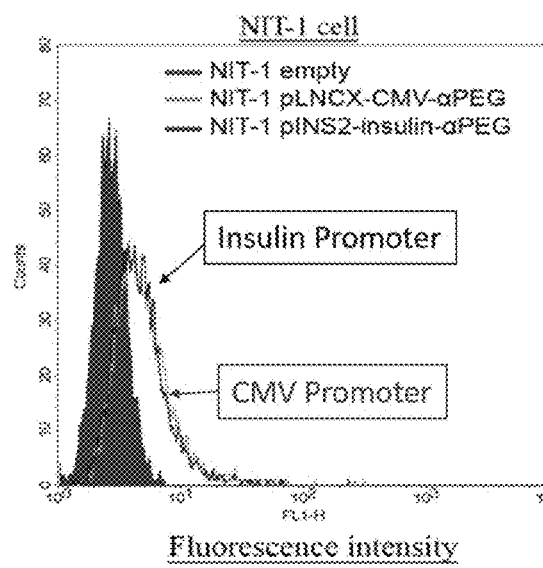
FIGS. 2A and 2B show the in vitro expression of pIns-anti-PEG reporter and the function thereof. The anti-PEG reporter gene was transferred into a plasmid having human insulin promoter to construct the pIns-anti-PEG plasmid (the control group is CMV promoter-anti-PEG plasmid). The genes was transferred into 2A mouse pancreatic islet beta cells (NIT-1) or 2B mouse fibroblast cells (3T3). The expression and function of the anti-PEG reporter in said two cells were detected by PEG-Quantum dot.
Figure 2B:
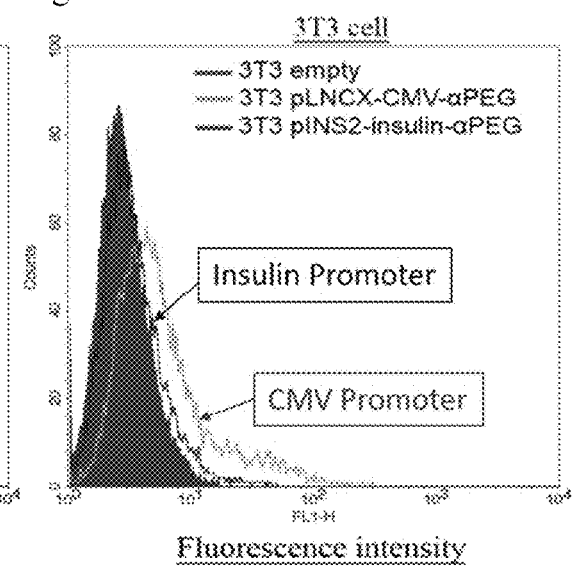
Figure 2B:
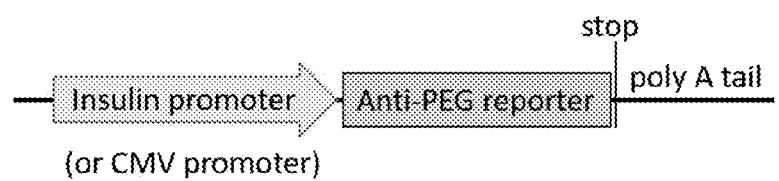

Example 2 Evaluation of Specific Expression of the Invention in Mouse Pancreatic Beta Cell To evaluate whether the functional anti-PEG reporter could specifically express on mouse pancreatic islet beta cells, the pIns-αPEG plasmid was transfected into mouse pancreatic islet beta cells (NIT-1) or mouse fibroblast cells (3T3). A fluorescent probe modified by PEG (PEG-Qdot) was used to verify that under regulation of the human insulin promoter, functional anti-PEG reporter can be specifically expressed on mouse pancreatic islet beta cells (NIT-1) (FIG. 2A), while it cannot express on mouse fibroblast cells (3T3) (see FIG. 2B).

Example 3 Preparation of NOD/pIns-αPEG Mouse of the Invention

To construct the NOD mice with pancreatic islet cells specifically expressing anti-PEG reporter (NOD/pIns-αPEG mice), the pIns-αPEG plasmid was digested with Nsi 1 and Not 1 enzymes to isolate pIns-αPEG gene fragment, and then, the pIns-αPEG gene fragment was transfected into the fertilized egg of the NOD mice using microinjection technique to produce NOD/pIns-αPEG mice (F0).

Figure 3:
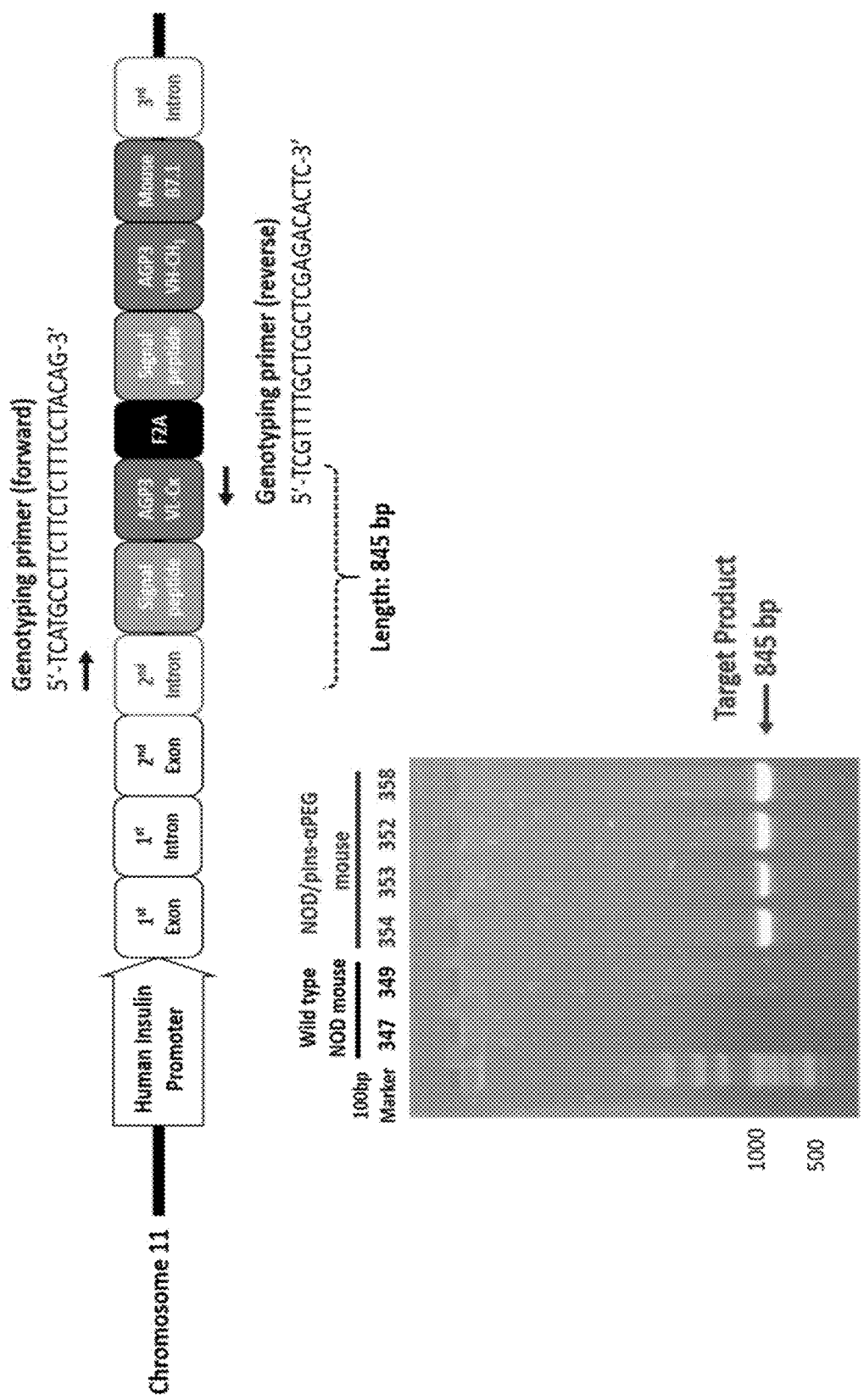
FIG. 3 shows the results of genotyping PCR check for identifying the NOD/pIns-αPEG mouse. The genotyping primer (forward) was designed to bind to the $2^{nd}$ intron of the human insulin gene. The genotyping primer (reverse) was designed to bind to the VL-CK fragment of the anti-PEG reporter gene. By using PCR method combined with these genotyping primers can produce a DNA fragment with an expected size of 845 bp in NOD/pIns-αPEG mice (No. 354, 353, 352, 258) but not in wild type NOD mice (No. 347, 349).

The genotyping check was used to confirm that the NOD mouse carries out the pIns-αPEG gene. Genomic DNA of NOD mice was isolated by a Easy Tissue and Cell Genomic DNA Purification Kit (GeneMark DP021E). The following locating primers, forward primer 5'-TCATGCCTTCT-TCTCTTTCCTACAG-3' (SEQ ID NO: 8) and reverse primer 5'-TCGTTTTGCTCGCTCGAGACACTC-3' (SEQ ID NO: 9) were used to confirm the NOD mouse brings the pIns-αPEG gene by PCR technology using a 2×Taq PCR Mix Red reagent (Bioman, RT803R). The PCR Condition shows as followed: (1) Initial Denaturation: 94° C. for 3 minutes; (2) Gene Amplification (repeated for 35 Cycles), a. Denaturation: 94° C. for 30 seconds, b. Annealing: 62° C. for 30 seconds, c. Extension: 72° C. for 60 seconds; (3) Final Extension: 72° C. for 10 minutes; (4) Storage at 4° C. Only NOD/pIns-αPEG mice has a 850 bp of PCR product, whereas the wild type NOD mice does not. FIG. 3 shows that the NOD/pIns-αPEG mice has a 850 bp of PCR product.

Figure 4:
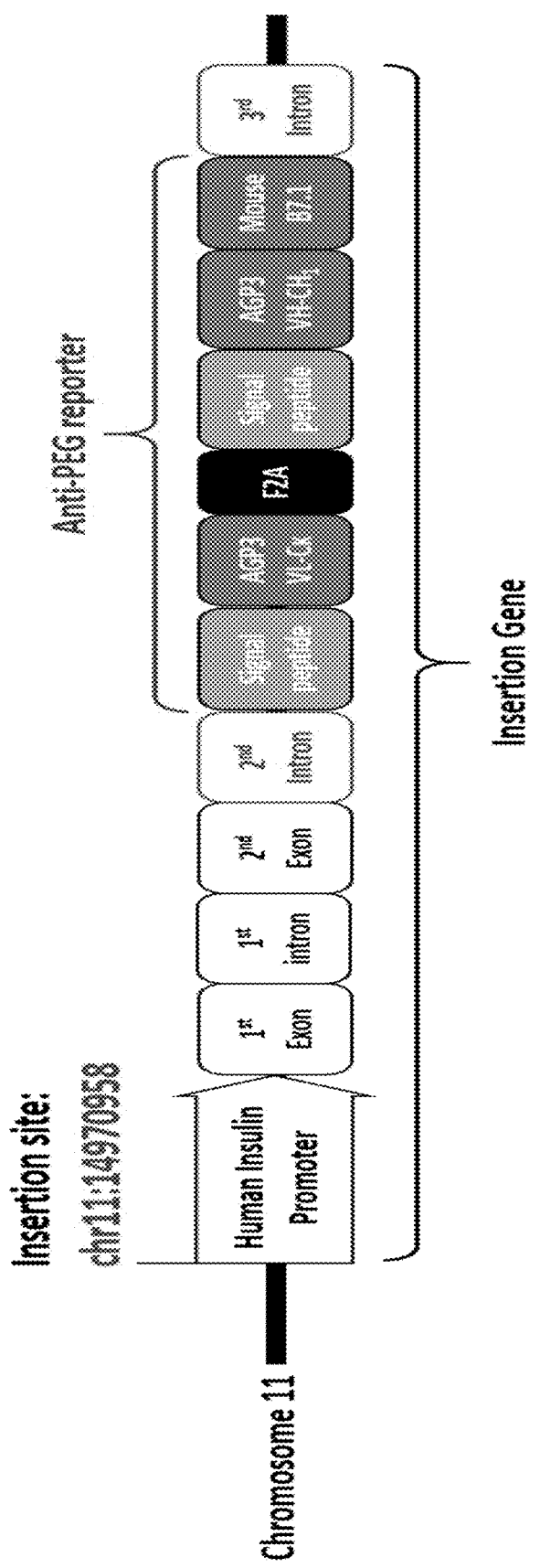
FIG. 4 shows insertion site of the transgenic gene construct in the genome of the NOD/pIns-αPEG mouse. The transgenic gene construct of the invention incorporated into a site at chromosome 11 of the mouse. In one embodiment, the site is chr11:14970958 at chromosome 11 of the mouse.
Figure 5:
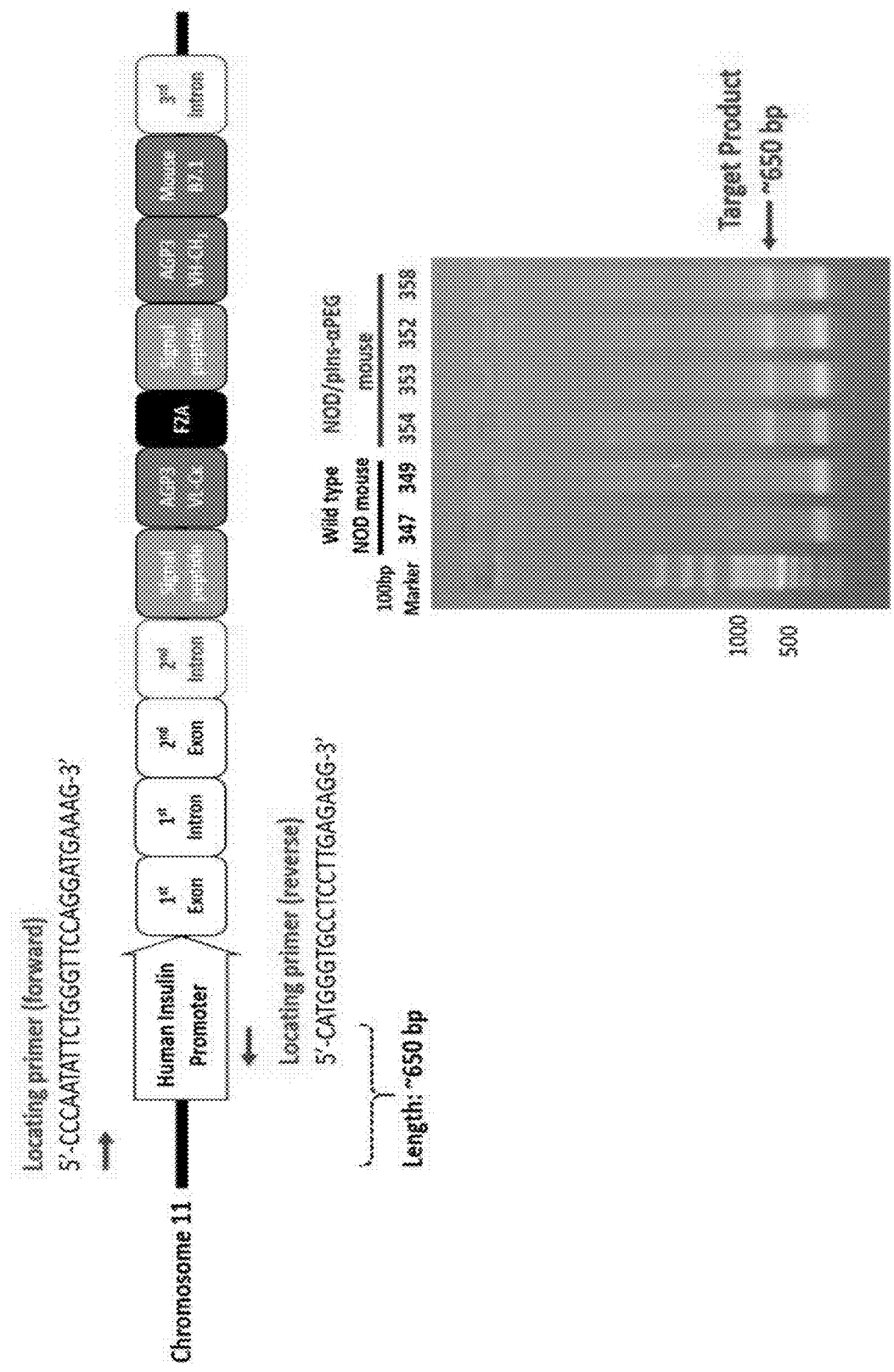
FIG. 5 shows the results of locating PCR check for identifying the insertion site of pIns-αPEG gene at the NOD/pIns-αPEG mouse. The locating primer (forward) was designed to bind to the chromosome 11 of the NOD mouse. The locating primer (reverse) was designed to bind to the human insulin promoter. By using PCR method combined with these locating primers can produce a DNA fragment with a size about 650 bp in NOD/pIns-αPEG mice (No. 354, 353, 352, 258) but not in wild type NOD mice (No. 347, 349).

The locating PCR check was used to confirm the insertion of transgenic gene construct of Example 1 to the site at the NOD mouse genome. Genomic DNA of NOD mice was isolated by a Easy Tissue and Cell Genomic DNA Purification Kit (GeneMark DP021E). The following locating primers, forward primer 5'-CCCAATATTCTGGGTTCCAG-GATGAAAG-3' (SEQ ID NO: 10) and reverse primer 5'-CATGGGTGCCTCCTTGAGAGG-3' (SEQ ID NO: 11), were used to confirm that the pIns-αPEG gene locates at chr11:14970958 site of chromosome 11 of the NOD mouse (see FIG. 5) by PCR technology using a SuperRed PCR Master Mix reagent (2×) (TOOLS TE-SR01). The PCR Condition shows as followed: (1) Initial Denaturation: 95° C. for 2 minutes; (2) Gene Amplification (repeated for 35 Cycles), a. Denaturation: 95° C. for 35 seconds, b. Annealing: 55° C. for 35 seconds, c. Extension: 72° C. for 2.5 minutes; (3) Final Extension: 72° C. for 10 minutes; (4) Storage at 4° C. The PCR results show that NOD/pIns-αPEG mice has a 650 bp of PCT product, so it confirms that the pIns-αPEG gene inserts to chromsome 11 of the NOD mice (chr11:14970958). The insertion site of the transgenic gene construct in the genome of the NOD mouse is shown in FIG. 4.

Figures 6A, 6B:
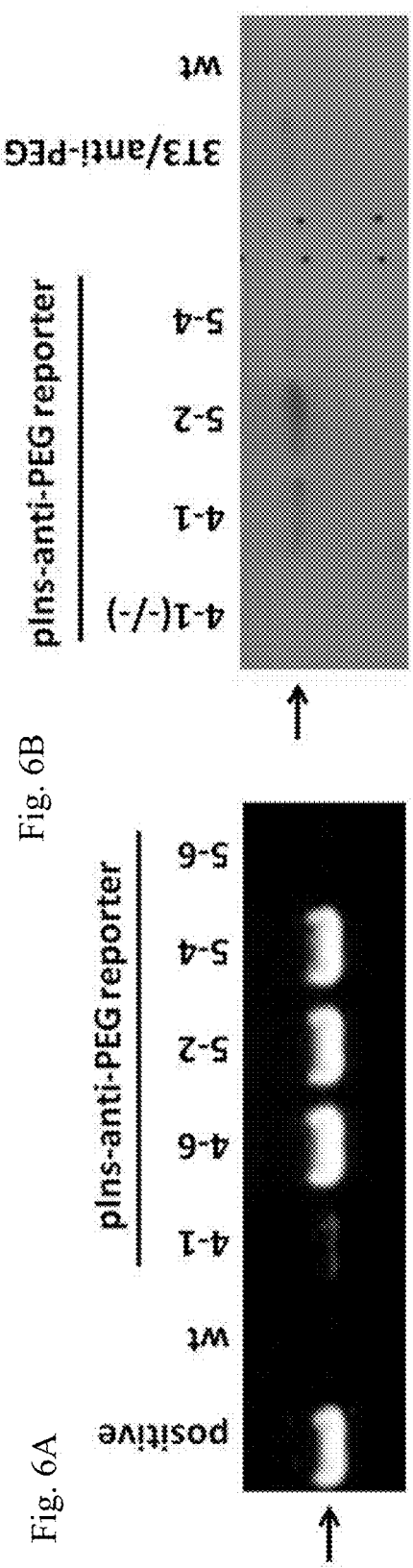
FIGS. 6A and 6B show the expression of anti-PEG reporter gene and the protein thereof in NOD/pIns-αPEG mice. The pIns-αPEG gene was transferred into the embryo of NOD/ShiLtJ mice by the microinjection technique (the embryo is from the Jackson Laboratory, stock number: 001976) to produce NOD/pIns-αPEG mice. 6A The transgenic mice expressing the anti-PEG reporter gene were identified and screened by genotyping PCR. 6B The progeny (F0) of NOD/pIns-αPEG mice numbered 4-1, 5-2 and 5-4 were analyzed to see if the islets thereof stably express the protein of anti-PEG reporter; the islet cells of the transgenic mice were obtained and subjected to western blot assay with goat anti-mouse IgM Fc antibody (the anti-PEG reporter is constructed by mouse IgM antibodies).

After genotype analysis, it shows that the NOD transgenic mice carried the anti-PEG reporter gene (FIG. 6A). Furthermore, the pancreatic islet cells of the progeny of the NOD/pIns-αPEG mice can stably express anti-PEG reporter protein by Western blot assay (see FIG. 6B). The above results show that the anti-PEG reporter gene of the F0 transgenic mice is successfully hereditable to the progeny.

Figure 7:
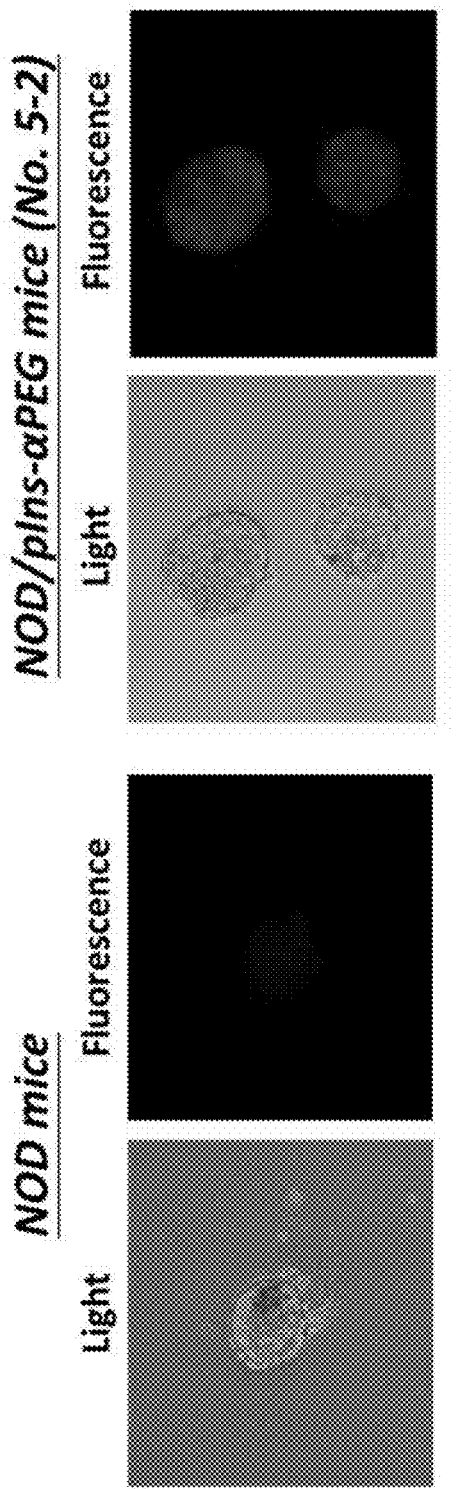
FIG. 7 shows the in vivo function of pIns-anti-PEG reporter (in the islet cells of NOD/pIns-αPEG mice). The islet cells were obtained from the NOD/pIns-αPEG mice (the progeny of the transgenic mice numbered 5-2) or NOD mice at the age of 5 weeks. The PEG-FITC fluorescent probe and fluorescent microscope were used to observe the binding ability of the islet cells and the PEG-probe.
Figure 8:
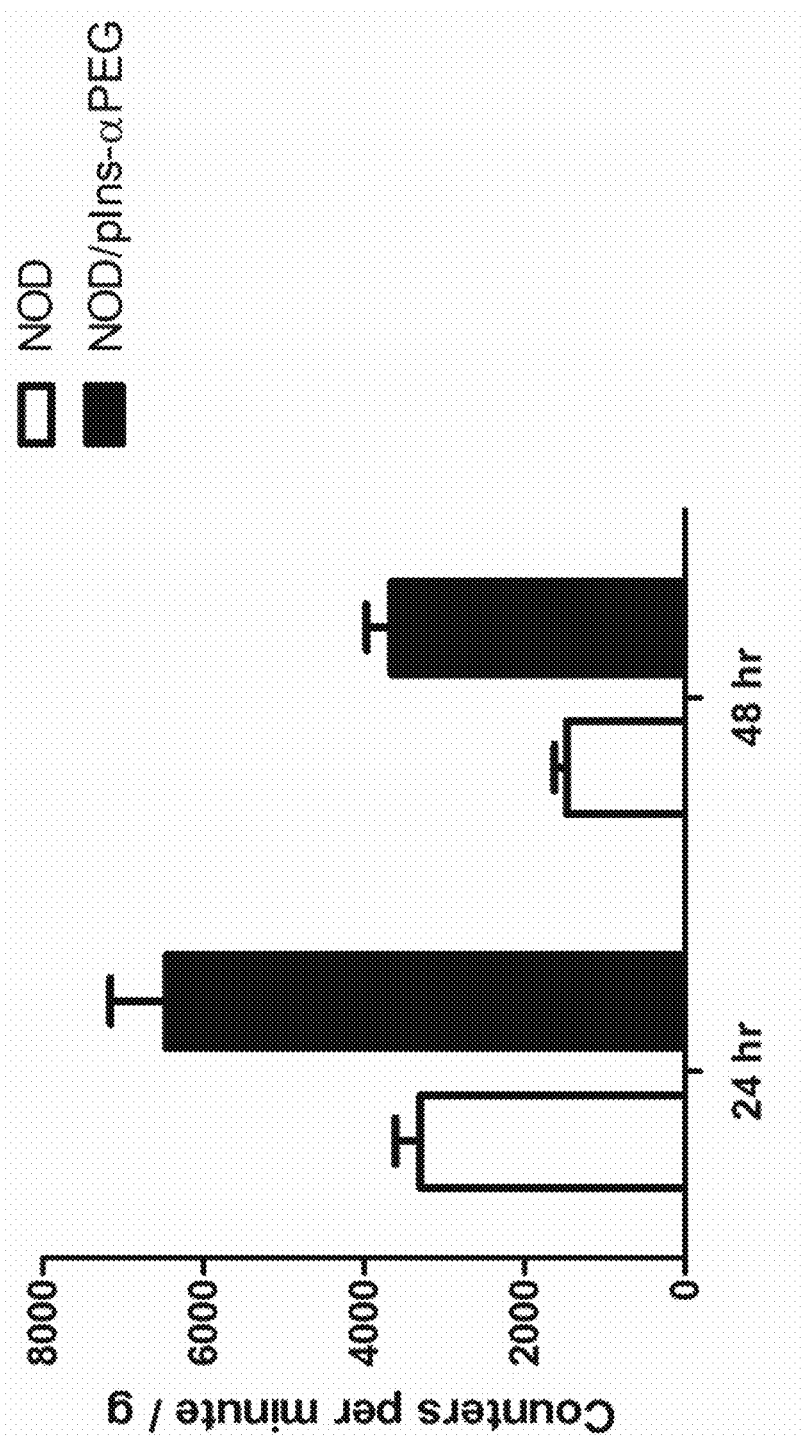
FIG. 8 shows the comparison on the difference in the accumulation of PEG-$^{131}$I in the pancreas of NOD/pIns-αPEG mice or NOD mice. PEG-$^{131}$I radioactive probe was intravenously injected into NOD/pIns-αPEG mice (n=3) or NOD mice (n=3), and their pancreas were taken after 24 and 48 hours, respectively. The radioactivity value of the area around the pancreas was detected with a gamma counter.

We further used fluorescence microscope to prove that PEG-FITC fluorescent probe can specifically bind to the pancreatic islet cells of NOD/pIns-αPEG mice rather than those of the control NOD mice (see FIG. 7). We used PEG-$^{131}$I and gamma counter to detect the anti-PEG reporter expression level of three NOD/pIns-αPEG mice. The results show that after administering PEG-$^{131}$I to the mice at 24 and 48 hours, the radiation values at pancreas of the NOD/pIns-αPEG mice are 1.96 folds and 2.48 folds higher than the control NOD mice (see FIG. 8).

Figure 9:
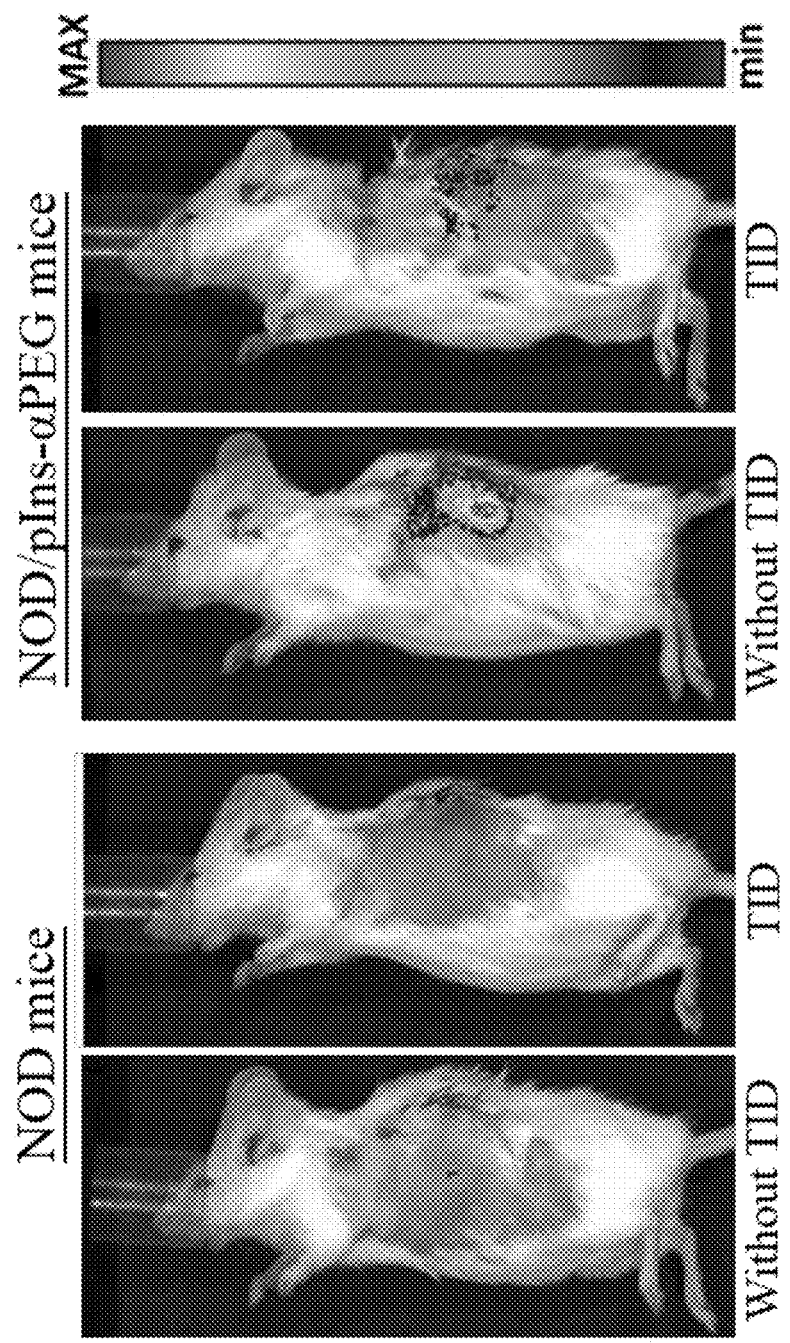
FIG. 9 shows the optical imaging of the pancreas of NOD/pIns-αPEG mice. 4-arm PEG-NIR797 (5 μg/20 μL/mouse) was injected into NOD/pIns-αPEG mice or NOD mice through pancreatic injection. After 24 hours, the specific fluorescent signal of anti-PEG reporter around the area of the pancreas was detected by a 3D in vivo imaging system (IVIS 200).

Example 4 Specifically Binding of PEG-Imaging Agent to Pancreatic Islet Cells Expressing Anti-PEG Reporter To test whether PEG-imaging agent can specifically bind to pancreatic islet cells expressing anti-PEG reporter, florescent imaging agent, 4-arm PEG-NIR797 was injected into pancreas of NOD/pIns-αPEG mice with type 1 diabetes (T1D) and NOD/pIns-αPEG mice without T1D, respectively. After 24 hours, optical imaging system, IVIS200 optical imaging system, was used to evaluate apoptosis of pancreatic islet cells. FIG. 9 shows that 4-arm PEG-NIR797 imaging agent can specifically accumulate in NOD/pIns-αPEG mice without T1D, while that cannot accumulate in NOD/pIns-αPEG mice with T1D. Moreover, since wild type NOD mice did not express anti-PEG reporter, no 4-arm PEG-NIR797 imaging agent was accumulated in the pancreatic islet cells.

Figure 10A:
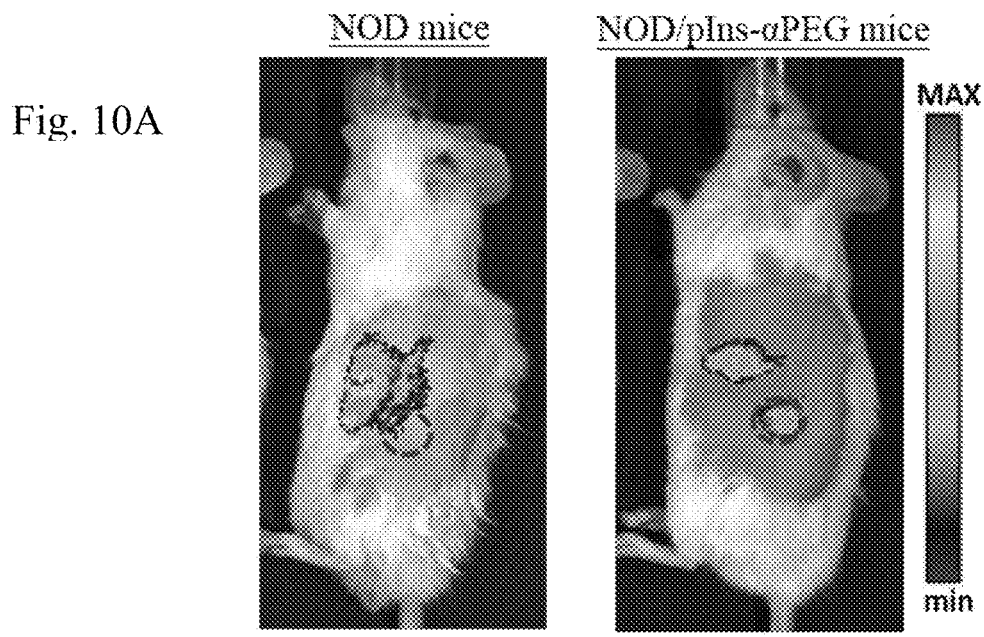
FIGS. 10A, 10B, and 10C show the viability of the islets of NOD/pIns-αPEG mice detected by non-invasive imaging. 4-arm PEG-NIR797 (50 μg/100 μL/mouse) was injected into healthy NOD mice (at the age of 10 weeks, as negative control, the left) and NOD/pIns-αPEG mice (at the age of 10 weeks, the right) through intraperitoneal injection. After 24 hours keeping from light, the viability of the islets in the pancreas of NOD/pIns-αPEG mice was observed by a 3D in vivo imaging system (IVIS 200). (A) Results of the non-invasive imaging. (B) Opening the abdominal cavity of the NOD mice and NOD/pIns-αPEG mice and evaluating the accumulation of 4-arm PEG-NIR797 therein. (C) The results of imaging the 4-arm PEG-NIR797 in the pancreas of NOD mice and NOD/pIns-αPEG mice.
Figure 10B:
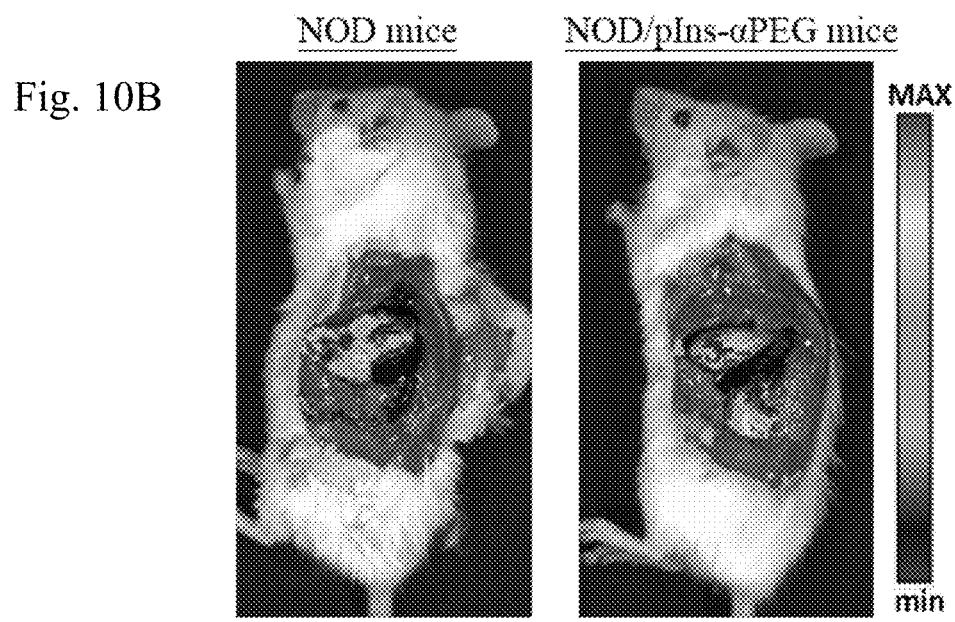
Figure 10C:
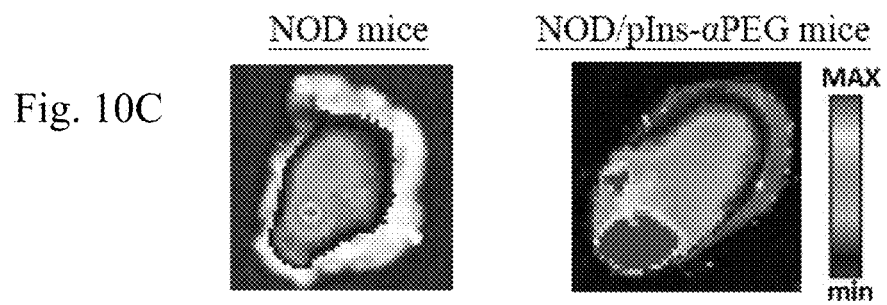
Figure 11B:
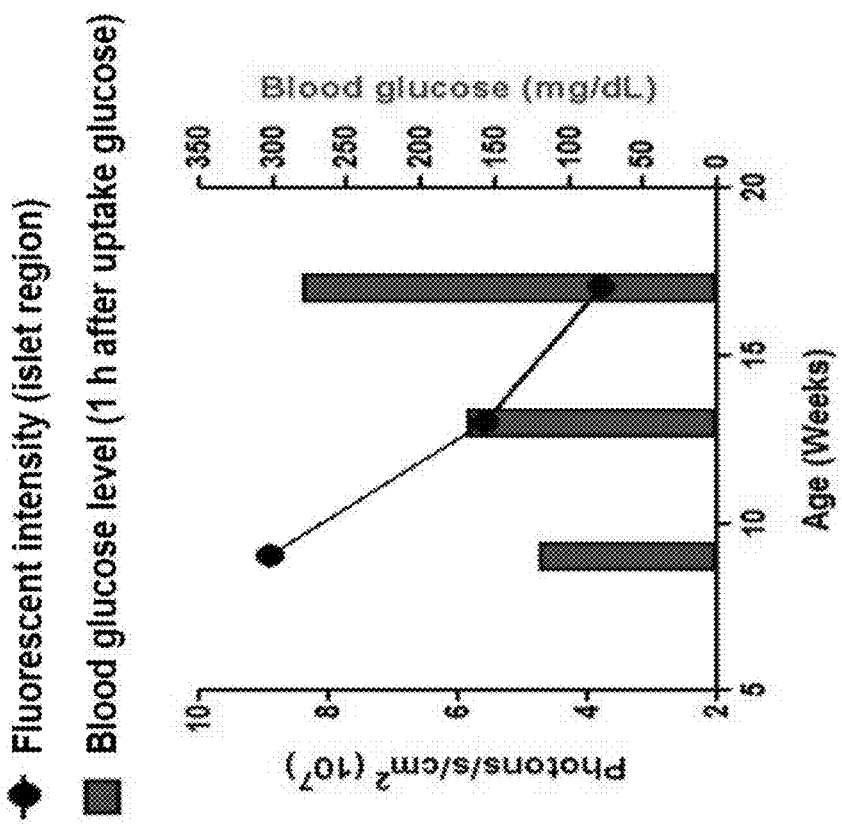
FIGS. 11A and 11B show the apoptosis of the islets of NOD/pIns-αPEG mice traced by non-invasive imaging. 11A 4-arm PEG-NIR797 (50 μg/100 μL/mouse) was injected into NOD/pIns-αPEG mice for every two weeks after the age of 9 weeks. After 24 hours keeping from light, the apoptotic process of the islets of NOD/pIns-αPEG mice at different age of weeks was observed by a 3D in vivo imaging system (IVIS 200). 11B The fluorescent signal of islets of NOD/pIns-αPEG mice at the age of 9, 13 and 17 weeks was measured, and the quantified values are expressed as the bars in the figure. In addition, to evaluate if the apoptotic process of the islets of NOD/pIns-αPEG mice demonstrated by the imaging system correlates with the ability to metabolize glucose (the weaker the fluorescent signal in the islets, the worse the ability to metabolize glucose/blood glucose), glucose of 1.5 g/kg/BW is orally administered to the NOD/pIns-αPEG mice which have been under fasting for 8 hours. After 1 hour of the administration, blood is obtained from the tail of the mice, and the blood glucose concentration is detected. High concentration of blood glucose represents insufficient secretion of insulin (i.e., the number of islets is insufficient), which may represents the severity of Type I diabetes.
Figure 11A:
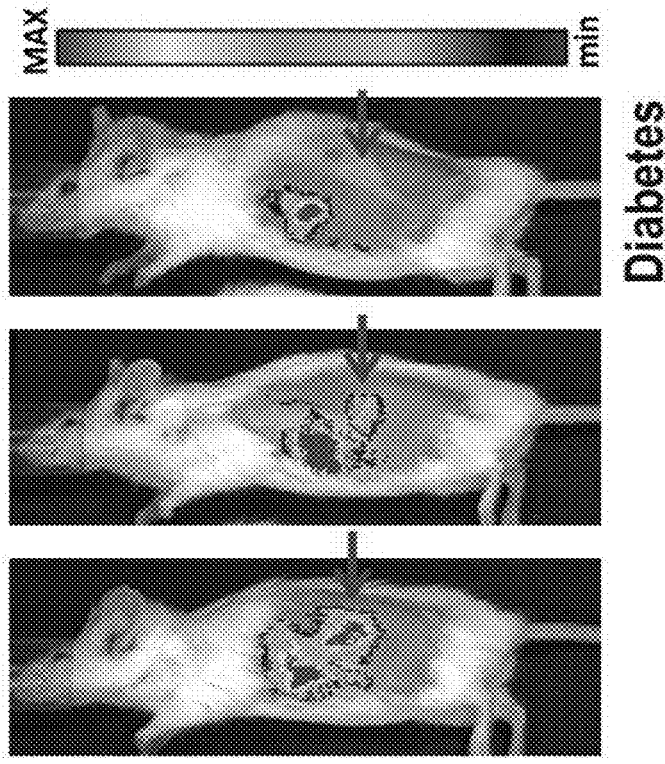

We further prove that after intraperitoneal injection of 4-arm NIR797 imaging agent to health NOD/pIns-αPEG mice and wild type NOD mice, 4-arm NIR797 imaging agent only accumulates in health pancreatic islet cells of NOD/pIns-αPEG mice but not wild type NOD mice (see FIG. 10). Finally, we prove that intraperitoneal injection of 4-arm NIR797 imaging agent in combination with optical imaging system, the apoptosis progress of pancreatic islets of NOD/pIns-αPEG mice at different weeks can be accurately and continuously traced (see FIG. 11A), and that the strength of the fluorescent signal emitted from pancreatic islets is highly correlated with the progress of T1D (see FIG. 11B).

Figure 12A:
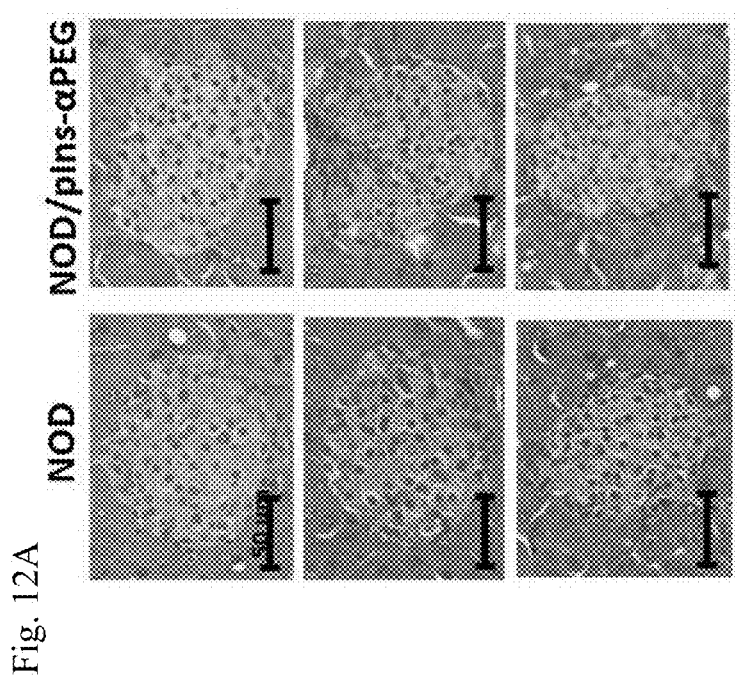
FIGS. 12A and 12B show the comparison of the size and numbers of the islets in the wild-type NOD mice and NOD/pIns-αPEG mice. The pancreatic tissues of wild-type NOD mice and NOD/pIns-αPEG mice (n=5) were collected at the age of 10 weeks. 12A The pancreatic tissues were stained by H&E staining, and comparing the islets of pancreas of the wild-type NOD mice and NOD/pIns-αPEG mice. 12B The average size of the islets was measured. 12C The average numbers of the islets were measured. Bar: SD.
Figure 12B:
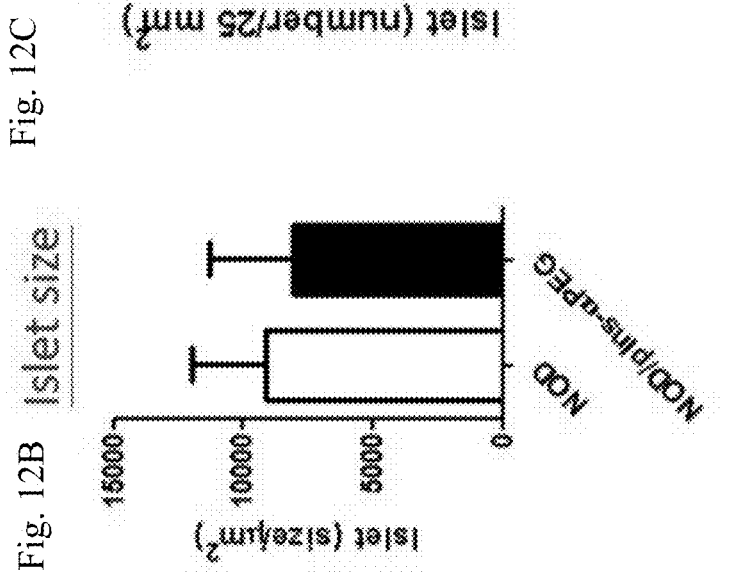
Figure 12C:
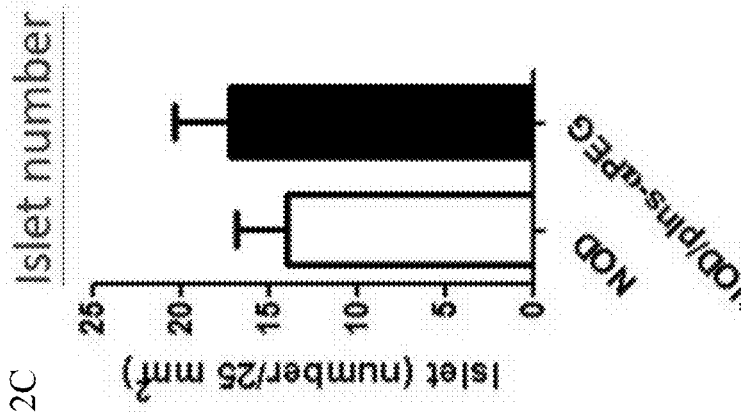
Figures 13A, 13B:
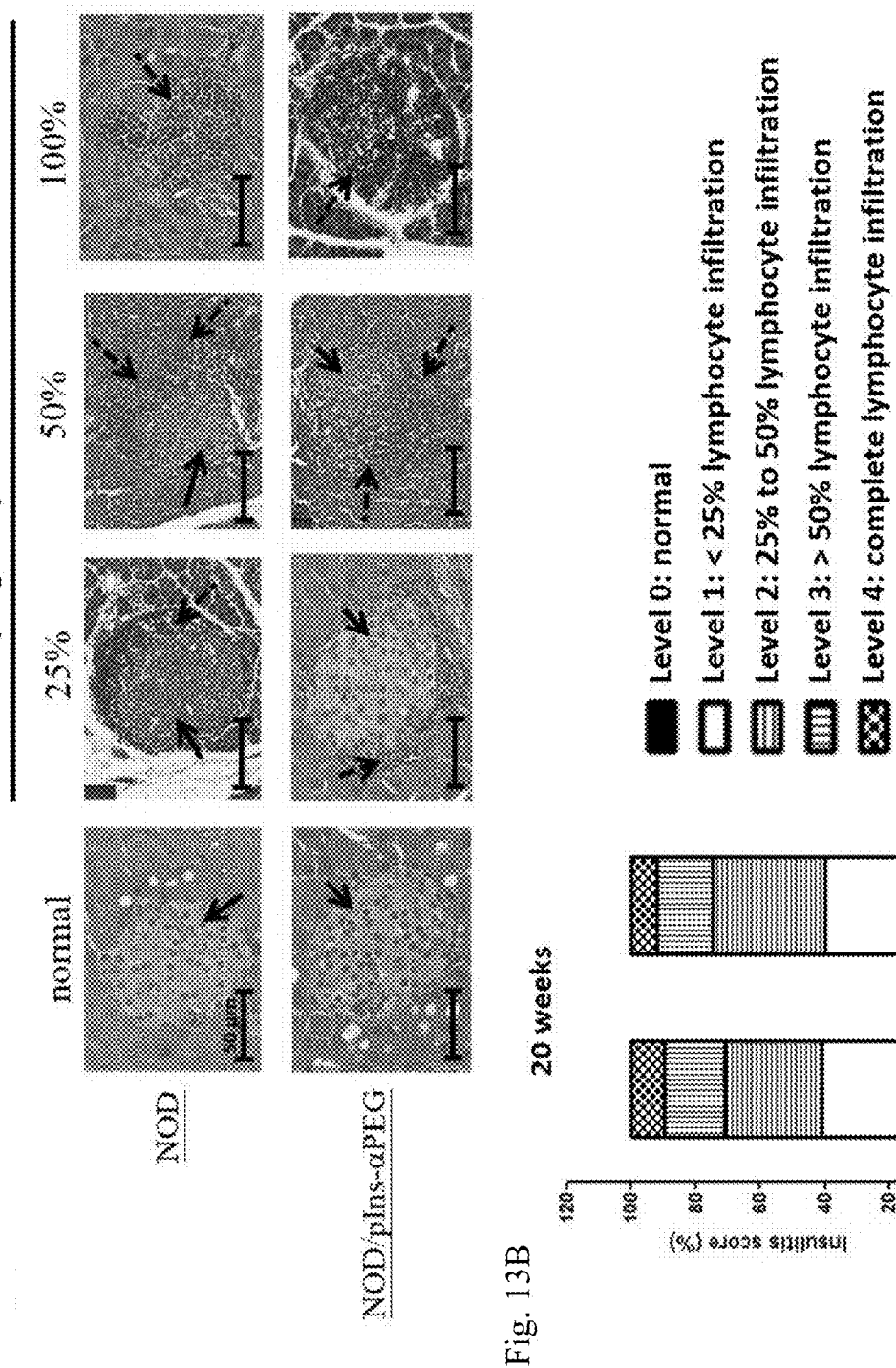
FIGS. 13A and 13B show the immune cells infiltration of pancreatic islets in wild-type NOD mice and NOD/pIns-αPEG mice. The pancreatic tissues of wild-type NOD mice and NOD/pIns-αPEG mice (n=5) were collected at the age of 20 weeks. 13A The pancreatic tissues were stained by H&E staining. The difference of immune cells infiltration between pancreatic islets in wild-type NOD mice and NOD/pIns-αPEG mice was observed. The arrows having solid line indicate islets, and the arrows having dotted lines indicate immune cells. 13B Quantifying the immune cells infiltration of pancreatic islets.
Figure 14:
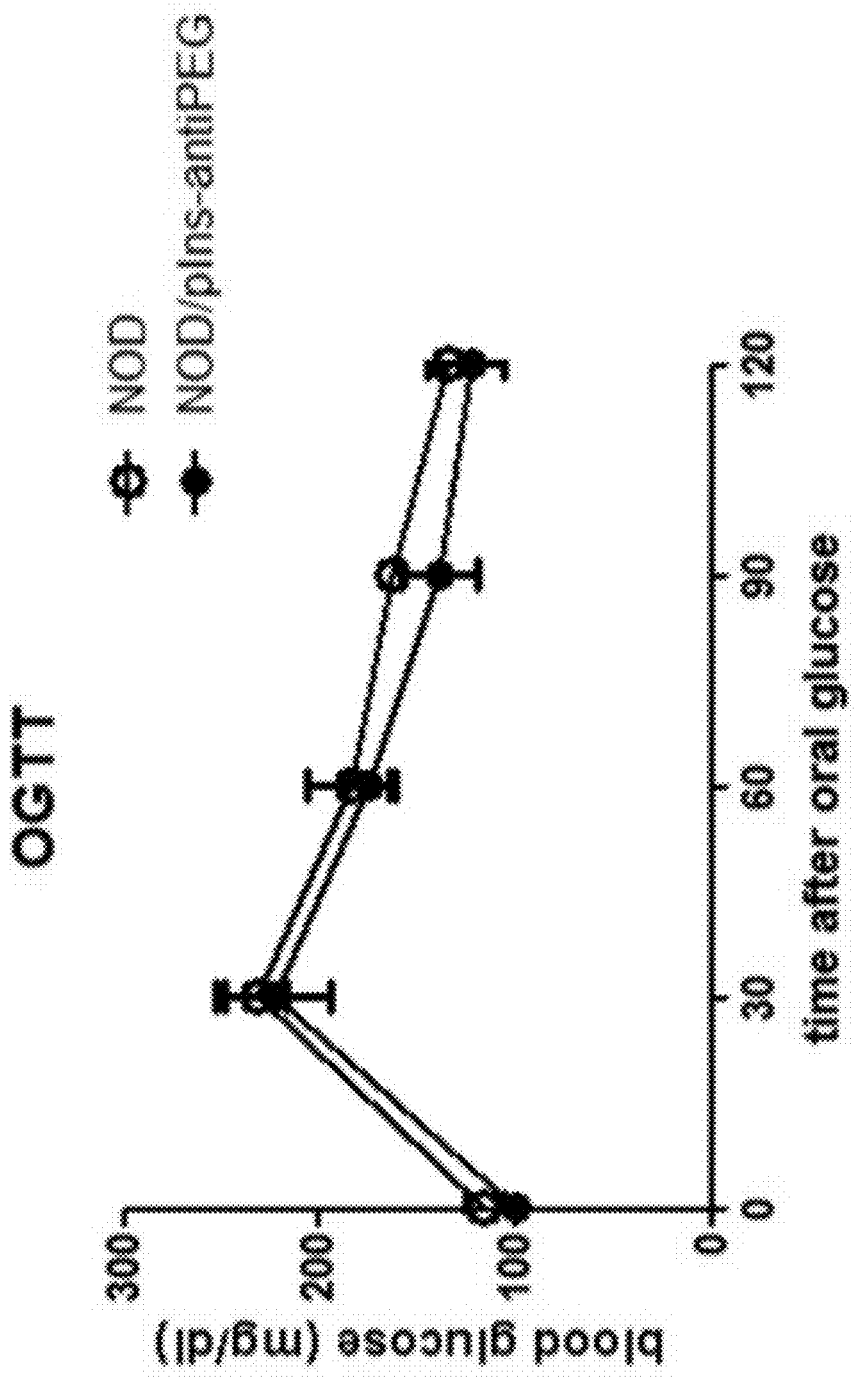
FIG. 14 shows the ability of the islet β cells of NOD/pIns-αPEG mice to secrete insulin. The wild-type NOD mice and NOD/pIns-αPEG mice (n=5) were fasting for 8 hours, and glucose of 1.5 g/kg/BW was orally administered to the mice. Blood was obtained from the tail of the mice at 0, 30, 60, 90 and 120 minutes after administration and the blood glucose concentration is detected to evaluate whether the anti-PEG reporter expressed on the cell membrane of the islet β cells may affect the secretion of insulin. Bar: SD.
Figure 15A:
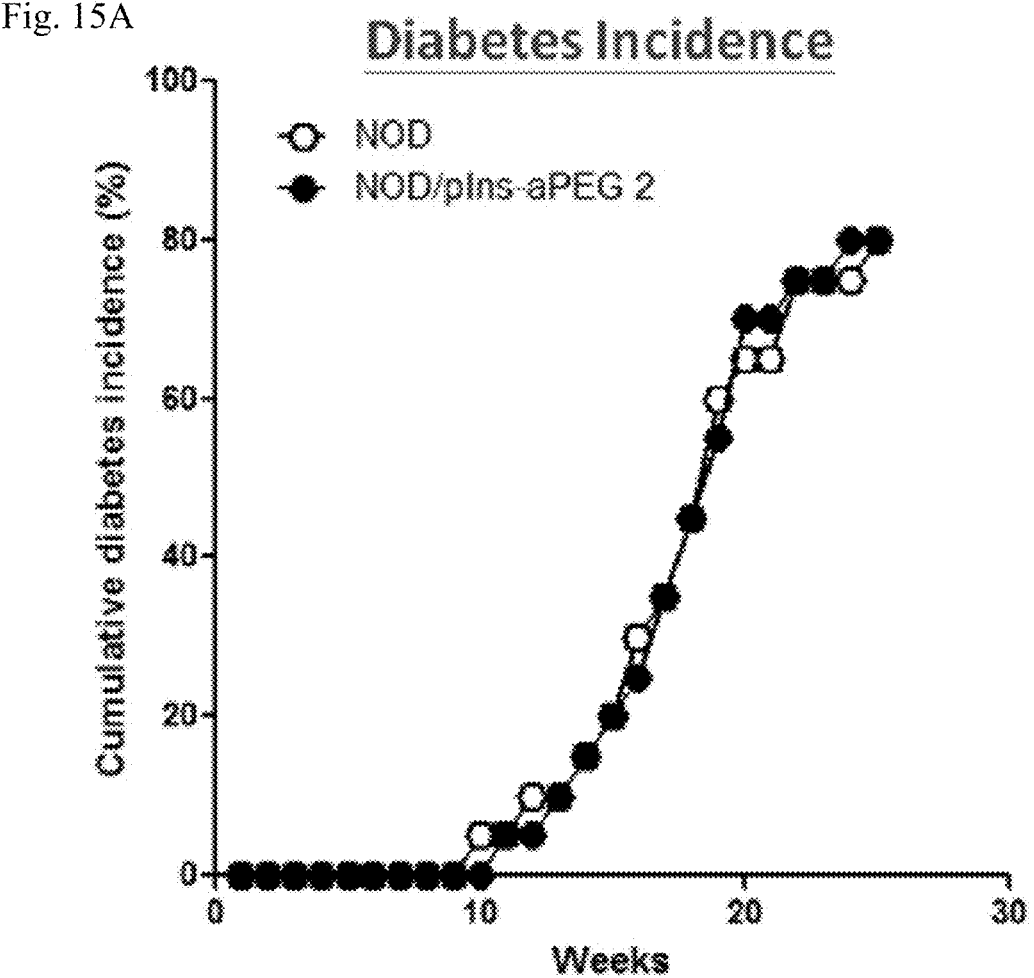

Example 5 Evaluation of Physiological Features and Pathological Features Based on Pancreatic Islets of NOD/pIns-αPEG Mice To evaluate whether the physiological features and pathological features of pancreatic islets of NOD/pIns-αPEG mice may be affected by anti-PEG reporter expression, histochemical stain assay was performed. It is proved that the morphology (see FIG. 12A), size (see FIG. 12B) and number (see FIG. 8C) of pancreatic islets of NOD/pIns-αPEG mice have no difference from those of the control NOD mice. For the NOD/pIns-αPEG mice and the control NOD mice at the age of 20 weeks, there is no difference in immune cell infiltration of pancreatic islets (see FIG. 13). The glucose metabolic rate of the NOD/pIns-αPEG mice is similar to that of the control NOD mice (see FIG. 14). Furthermore, the T1D progress (see FIG. 15A) and the onset of the immune reaction (see FIG. 15B) of anti-insulin antibody of the NOD/pIns-αPEG mice are the same as those of the control NOD mice.

I claim:

1. A transgenic gene construct encoding an anti-PEG reporter, the gene construct comprising a polynucleotide comprising, from 5' to 3' sequence: a human insulin promoter having the nucleotide sequence of SEQ ID NO:1, a first exon of human insulin gene having the nucleotide sequence of SEQ ID NO:2, a first intron of human insulin gene having the nucleotide sequence of SEQ ID NO:3, a second exon of human insulin gene having the nucleotide sequence of SEQ ID NO: 4, a second intron of rabbit beta globin gene having the nucleotide sequence of SEQ ID NO:5, an anti-PEG reporter gene having the nucleotide sequence of SEQ ID NO:6 and a third intron of rabbit beta globin gene having the nucleotide sequence of SEQ ID NO:7, which are operably linked to each other.

2. The transgenic gene construct of claim 1, wherein the nucleotide sequence is a degenerate sequence.

3. A vector comprising the transgenic gene construct of claim 1.

4. An isolated cell comprising the vector of claim 3.

5. A transgenic NOD mouse, wherein the genome of the NOD mouse comprises a transgenic gene construct of claim 1, wherein the anti-PEG reporter gene is expressed in pancreatic islets.

6. The transgenic NOD mouse of claim 5, wherein the transgenic gene construct is incorporated into a site at chromosome 11 of the mouse.

7. The transgenic NOD mouse of claim 6, wherein the transgenic gene construct is incorporated into the site chr11: 14970958 at chromosome 11.

8. A method for generating a transgenic NOD mouse of claim 5, comprising the steps of:
  1) microinjecting the transgenic gene construct of claim 1 into fertilized eggs of a NOD mouse to prepare transfected fertilized eggs; and
  2) implanting the transfected fertilized egg into a pseudopregnant mouse;
  wherein the anti-PEG reporter gene is expressed in pancreatic islets, and wherein said implanting produces a transgenic NOD mouse.

* * * * *

SEQUENCE LISTING

<160> NUMBER OF SEQ ID NOS: 11

<210> SEQ ID NO 1
<211> LENGTH: 1620
<212> TYPE: DNA
<213> ORGANISM: human
<220> FEATURE:
<221> NAME/KEY: misc_feature
<222> LOCATION: (601)..(601)
<223> OTHER INFORMATION: n is a, c, g, or t
<220> FEATURE:
<221> NAME/KEY: misc_feature
<222> LOCATION: (607)..(607)
<223> OTHER INFORMATION: n is a, c, g, or t
<220> FEATURE:
<221> NAME/KEY: misc_feature
<222> LOCATION: (610)..(610)
<223> OTHER INFORMATION: n is a, c, g, or t
<220> FEATURE:
<221> NAME/KEY: misc_feature
<222> LOCATION: (617)..(617)
<223> OTHER INFORMATION: n is a, c, g, or t
<220> FEATURE:
<221> NAME/KEY: misc_feature
<222> LOCATION: (646)..(646)
<223> OTHER INFORMATION: n is a, c, g, or t
<220> FEATURE:
<221> NAME/KEY: misc_feature
<222> LOCATION: (666)..(666)
<223> OTHER INFORMATION: n is a, c, g, or t
<220> FEATURE:

```
<221> NAME/KEY: misc_feature
<222> LOCATION: (679)..(679)
<223> OTHER INFORMATION: n is a, c, g, or t
<220> FEATURE:
<221> NAME/KEY: misc_feature
<222> LOCATION: (695)..(695)
<223> OTHER INFORMATION: n is a, c, g, or t
<220> FEATURE:
<221> NAME/KEY: misc_feature
<222> LOCATION: (708)..(708)
<223> OTHER INFORMATION: n is a, c, g, or t
<220> FEATURE:
<221> NAME/KEY: misc_feature
<222> LOCATION: (1054)..(1054)
<223> OTHER INFORMATION: n is a, c, g, or t

<400> SEQUENCE: 1
gatcctggat ctcagctccc tggccgacaa cactggcaaa ctcctactca tccacgaagg      60
ccctcctggg catggtggtc cttcccagcc tggcagtctg ttcctcacac accttgttag     120
tgcccagccc ctgaggttgc agctgggggt gtctctgaag ggctgtgagc ccccaggaag     180
ccctggggaa gtgcctgcct tgcctccccc cggccctgcc agcgcctggc tctgccctcc     240
tacctgggct cccccatcc agcctccctc cctacacact cctctcaagg aggcacccat     300
gtcctctcca gctgccgggc tcagagcac tgtggcgtcc tggggcagcc accgcatgtc     360
ctgctgtggc atggctcagg gtggaaaggg cggaagggag gggtcctgca gatagctggt     420
gcccactacc aaacccgctc ggggcaggag agccaaaggc tgggtgtgtg cagagcggcc     480
ccgagaggtt ccgaggctga ggccagggtg ggacataggg atgcgagggg ccggggcaca     540
ggatactcca acctgcctgc ccccatggtc tcatcctcct gcttctggga cctcctgatc     600
ntgcccntgn tgataanagg caggtagggg ctgcaggcag cagggntcgg agcccatgcc     660
ccctcnccat gggtcaggnt ggacctccag gtgcntgttc tggggagntg ggagggccgg     720
aggggtgtac cccaggggct cagcccagat gacactatgg gggtgatggt gtcatgggac     780
ctggccagga gaggggagat gggctcccag aagaggagtg ggggctgaga gggtgcctgg     840
ggggccagga cggagctggg ccagtgcaca gcttcccaca cctgcccacc cccagagtcc     900
tgccgccacc cccagatcac acggaagatg aggtccgagt ggcctgctga ggacttgctg     960
cttgtcccca ggtccccagg tcatgccctc cttctgccac cctggggagc tgagggcctc    1020
agctggggct gctgtctaag gcagggtggg caantaaggc agccagcagg aggggacccc    1080
tccctcactc ccactctccc accccacca ccttggccca tccatggcgg catcttgggc    1140
catccgggac tggggacagg ggtcctgggg acagggtct gaggacaggg gtgtgggcac    1200
aggggtcctg gggacagggg tcctggggac aggggtcctg gggacagggg tctggggaca    1260
acagcgcaaa gaccccccc ctgcagcctc catctctcct ggtctaatgt ggaaagtggc    1320
ccaggtgagg gctttgctct cctggagaca tttgcccca gctgtgagca gggacaggtc    1380
tggccaccgg gcccctggtt aagactctaa tgcccgctg gtcctgagga agaggtgctg    1440
acgaccaagg agatcttccc acagccccag caccaggaa atggtccgga aattgcagcc    1500
tcagccccca gccatctgcc gacccccca ccccagccct aatgggccag gcggcagggg    1560
ttgacaggta ggggagatgg gctctgagac tataaagcca gcggggggcc agcagccctc    1620

<210> SEQ ID NO 2
<211> LENGTH: 42
<212> TYPE: DNA
<213> ORGANISM: human

<400> SEQUENCE: 2
```

```
agccctccag acaggctgc atcagaagag gccatcaagc ag                    42

<210> SEQ ID NO 3
<211> LENGTH: 178
<212> TYPE: DNA
<213> ORGANISM: human

<400> SEQUENCE: 3
gtctgttcca agggcctttg cgtcaggtgg gctcagggtt ccagggtggc tggacccccag   60 gccccagctc tgcagcaggg aggacgtggc tgggctcgtg aagcatgtgg gggtgagccc   120
aggggcccca aggcagggca cctgccttca gcctgcctca gccctgcctg tctcccag     178

<210> SEQ ID NO 4
<211> LENGTH: 50
<212> TYPE: DNA
<213> ORGANISM: human

<400> SEQUENCE: 4
atcactgtcc ttctgcacct gcagggatcg gggatcctga gaacttcagg               50

<210> SEQ ID NO 5
<211> LENGTH: 573
<212> TYPE: DNA
<213> ORGANISM: rabbit

<400> SEQUENCE: 5
gtgagtttgg ggaccccttga ttgttctttc ttttttcgcta ttgtaaaatt catgttatat   60 ggaggggggca aagttttcag ggtgttgttt agaatgggaa gatgtcccctt gtatcaccat   120 ggaccctcat gataattttg tttctttcac tttctactct gttgacaacc attgtctcct   180 cttatttttct tttcattttc tgtaactttt tcgttaaact ttagcttgca tttgtaacga   240
atttttaaat tcactttgtg ttatttgtca gattgtaagt actttctcta atcactttt    300 tttcaaggca atcagggtat attatattgt acttcagcac agttttagag aacaattgtt    360
ataattaaat gataaggtag aatatttctg catataaatt ctggctggcg tggaaatatt    420
cttattggta gaaacaacta caccctggtc atcatcctgc ctttctcttt atggttacaa    480
tgatatacac tgtttgagat gaggataaaa tactctgagt ccaaaccggg cccctctgct    540
aaccatgttc atgccttctt ctctttcta cag                                  573

<210> SEQ ID NO 6
<211> LENGTH: 2574
<212> TYPE: DNA
<213> ORGANISM: artificial
<220> FEATURE:
<223> OTHER INFORMATION: Anti-PEG reporter gene

<400> SEQUENCE: 6
atggagacag acacactcct gctatgggta ctgctgctct gggttccagg ttccactggt     60
gacggagggg ccgatattgt gttgacgcag gctgcattct ccaatccagt cactcttgga   120
acatcagctt ccatctcctg caggtctagt aagagtctcc tacatagtaa tggcatcact   180
tatttgtatt ggtatctgca gaagccaggc cagtctcctc agctcctgat ttatcagatg   240
tccaaccttg cctcaggagt cccagacagg ttcagtagca gtgggtcagg aactgatttc   300
acactgagaa tcagcagagt ggaggctgag gatgtgggtg tttattactg tgctcaaaat   360
ctagaactat tcacgttcgg ctcggggaca aagttggaaa taaaacgggc tgatgctgca   420
```

```
ccaactgtat ccatcttccc accatccagt gagcagttaa catctggagg tgcctcagtc      480
gtgtgcttct tgaacaactt ctaccccaaa gacatcaatg tcaagtggaa gattgatggc      540
agtgaacgac aaaatggcgt cctgaacagt tggactgatc aggacagcaa agacagcacc      600
tacagcatga gcagcaccct cacgttgacc aaggacgagt atgaacgaca taacagctat      660
acctgtgagg ccactcacaa gacatcaact tcacccattg tcaagagctt caacaggaat      720
gagtgttagc tcgagggatc cgcccctctc cctccccccc ccctaacgtt actggccgaa      780
gccgcttgga ataaggccgg tgtgcgtttg tctatatgtt attttccacc atattgccgt      840
cttttggcaa tgtgagggcc cggaaacctg gccctgtctt cttgacgagc attcctaggg      900
gtctttcccc tctcgccaaa ggaatgcaag gtctgttgaa tgtcgtgaag gaagcagttc      960
ctctggaagc ttcttgaaga caaacaacgt ctgtagcgac cctttgcagg cagcggaacc     1020
ccccacctgg cgacaggtgc ctctgcggcc aaaagccacg tgtataagat acacctgcaa     1080
aggcggcaca accccagtgc cacgttgtga gttggatagt tgtggaaaga gtcaaatggc     1140
tctcctcaag cgtattcaac aagggctgaa ggatgcccca aaggtaccc cattgtatgg      1200 gatctgatct ggggcctcgg tgcacatgct ttacatgtgt ttagtcgagg ttaaaaaaac     1260
gtctaggccc cccgaaccac ggggacgtgg ttttcctttg aaaaacacga tgataatatg     1320
gccacaacca tggagacaga cacactcctg ctatgggtac tgctgctctg ggttccaggt     1380
tccactggtg acagatctga agtgcagctg gtggagtctg ggggaggctt agtgaagcct     1440
ggagggtccc tgaaactctc ctgtgcagcc tctggattca ctttcagtga ctattacatg     1500
tattgggttc gccagactcc ggaaaagagg ctggagtggg tcgcaaccat tagtgatgat     1560
ggtacttaca cctactatcc acacagtgtg aagggcgat tcaccatctc cagagacagt     1620
gccaagaaca acctgtacct gcaattgagc agtctgaagt ctgaggacac agccatgtat     1680
tactgtgcaa gaaatgatgc tagggggggac tactggggtc aaggaacctc agtcaccgtc     1740
tcctcagaga gtcagtcctt cccaaatgtc ttccccctcg tctcctgcga gagcccctg      1800 tctgataaga atctggtggc catgggctgc ctggcccggg acttcctgcc cagcaccatt     1860
tccttcacct ggaactacca gaacaacact gaagtcatcc agggtatcag aaccttccca     1920
acactgagga caggggcaa gtacctagcc acctcgcagg tgttgctgtc tcccaagagc     1980
atccttgaag gttcagatga ataccTGgta tgcgaaatcc actacggagg caaaaacaga     2040
gatctgcatg tgcccattcc agctgtcgca gaggtcgacg ctgacttctc tacccccaac     2100
ataactgagt ctgaaacccc atctgcagac actaaaagga ttacctgctt tgcttccggg     2160
ggtttcccaa agcctcgctt ctcttggttg gaaaatggaa gagaattacc tggcatcaat     2220
acgacaattt cccaggatcc tgaatctgaa ttgtacacca ttagtagcca actagatttc     2280
aatacgactc gcaaccacac cattaagtgt ctcattaaat atggagatgc tcacgtgtca     2340
gaggacttca cctgggaaaa accccagaa gaccctcctg atagcaagaa cacacttgtg     2400
ctctttgggg caggattcgg cgcagtaata acagtcgtcg tcatcgttgt catcatcaaa     2460
tgcttctgta agcacagaag ctgtttcaga agaaatgagg caagcagaga aacaaacaac     2520
agccttacct tcgggcctga agaagcatta gctgaacaga ccgtcttcct ttag          2574
```

<210> SEQ ID NO 7
<211> LENGTH: 449
<212> TYPE: DNA
<213> ORGANISM: rabbit

<400> SEQUENCE: 7

```
gatctttttc cctctgccaa aaattatggg gacatcatga agccccttga gcatctgact        60
tctggctaat aaaggaaatt tatttttcatt gcaatagtgt gttggaattt tttgtgtctc      120
tcactcggaa ggacatatgg gagggcaaat catttaaaac atcagaatga gtatttggtt      180
tagagtttgg caacatatgc ccatatgctg gctgccatga acaaaggttg gctataaaga      240
ggtcatcagt atatgaaaca gcccctgct gtccattcct tattccatag aaaagccttg      300
acttgaggtt agatttttt tatattttgt tttgtgttat ttttttcttt aacatcccta      360
aaattttcct tacatgtttt actagccaga ttttttcctcc tctcctgact actcccagtc      420
atagctgtcc ctcttctctt atggagatc                                         449

<210> SEQ ID NO 8
<211> LENGTH: 25
<212> TYPE: DNA
<213> ORGANISM: artificial sequence
<220> FEATURE:
<223> OTHER INFORMATION: synthetic oligonucleotide

<400> SEQUENCE: 8
tcatgccttc ttctctttcc tacag                                              25

<210> SEQ ID NO 9
<211> LENGTH: 24
<212> TYPE: DNA
<213> ORGANISM: artificial sequence
<220> FEATURE:
<223> OTHER INFORMATION: synthetic oligonucleotide

<400> SEQUENCE: 9
tcgttttgct cgctcgagac actc                                               24

<210> SEQ ID NO 10
<211> LENGTH: 28
<212> TYPE: DNA
<213> ORGANISM: artificial sequence
<220> FEATURE:
<223> OTHER INFORMATION: synthetic oligonucleotide

<400> SEQUENCE: 10
cccaatattc tgggttccag gatgaaag                                           28

<210> SEQ ID NO 11
<211> LENGTH: 21
<212> TYPE: DNA
<213> ORGANISM: artificial sequence
<220> FEATURE:
<223> OTHER INFORMATION: synthetic oligonucleotide

<400> SEQUENCE: 11
catgggtgcc tccttgagag g                                                  21
```